(12) United States Patent
Karo et al.

(10) Patent No.: US 8,494,609 B2
(45) Date of Patent: Jul. 23, 2013

(54) BODY FAT MEASUREMENT DEVICE

(75) Inventors: Hiromichi Karo, Kyoto (JP); Takehiro Hamaguchi, Kyoto (JP); Kazuhisa Tanabe, Kyoto (JP); Yasuaki Murakawa, Kyoto (JP); Tomoya Ijiri, Kameoka (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/607,233

(22) Filed: Sep. 7, 2012

(65) Prior Publication Data
US 2013/0006086 A1  Jan. 3, 2013

Related U.S. Application Data

(63) Continuation of application No. PCT/JP2011/052762, filed on Feb. 9, 2011.

(30) Foreign Application Priority Data

Mar. 25, 2010  (JP) .................................. 2010-070374

(51) Int. Cl.
*A61B 5/053*  (2006.01)
(52) U.S. Cl.
USPC ........................... 600/382; 600/393; 600/547
(58) Field of Classification Search
USPC ........... 600/372, 382, 390, 393, 547; 439/909
See application file for complete search history.

(56) References Cited

U.S. PATENT DOCUMENTS

| | | | | |
|---|---|---|---|---|
| 5,785,665 | A  * | 7/1998 | Soejima | 600/594 |
| 6,472,617 | B1 * | 10/2002 | Montagnino | 177/126 |
| 7,184,822 | B2 * | 2/2007 | Kasahara et al. | 600/547 |

(Continued)

FOREIGN PATENT DOCUMENTS

| | | |
|---|---|---|
| JP | A-2001-212111 | 8/2001 |
| JP | A-2002-369806 | 12/2002 |

(Continued)

OTHER PUBLICATIONS

International Search Report issued in International Application No. PCT/JP2011/052762 dated Apr. 12, 2011 (with translation).

*Primary Examiner* — Lee S Cohen
*Assistant Examiner* — Erin M Cardinal
(74) *Attorney, Agent, or Firm* — Oliff & Berridge, PLC

(57) ABSTRACT

A body fat measurement device includes multiple electrodes, a trunk area width detection unit for measuring a trunk area width and a trunk area depth, a body impedance measurement unit that measures a body impedance of a body using the multiple electrodes, and a body fat mass calculation unit that calculates a body fat mass based on the measured body impedance and the trunk area width and trunk area depth. A frame-shaped fitting unit in which the trunk area width detection unit is provided and that is capable of being disposed so as to surround a measurement subject's trunk area can be mounted on and removed from a platform unit in which foot electrodes are provided, and is stored within the platform unit during a stored state.

12 Claims, 22 Drawing Sheets

U.S. PATENT DOCUMENTS

| | | | |
|---|---|---|---|
| 2002/0123695 A1* | 9/2002 | Kawanishi | 600/547 |
| 2003/0216665 A1* | 11/2003 | Masuo et al. | 600/547 |
| 2005/0059902 A1* | 3/2005 | Itagaki | 600/547 |
| 2005/0124909 A1* | 6/2005 | Kasahara et al. | 600/547 |
| 2005/0209528 A1* | 9/2005 | Sato et al. | 600/547 |
| 2006/0025701 A1* | 2/2006 | Kasahara | 600/547 |
| 2007/0038140 A1* | 2/2007 | Masuo et al. | 600/547 |
| 2008/0243026 A1* | 10/2008 | Tsuji | 600/547 |
| 2009/0024053 A1* | 1/2009 | Kasahara | 600/547 |
| 2009/0182243 A1* | 7/2009 | Oku et al. | 600/547 |
| 2012/0310068 A1* | 12/2012 | Karo et al. | 600/384 |

FOREIGN PATENT DOCUMENTS

| | | |
|---|---|---|
| JP | A-2005-288023 | 10/2005 |
| JP | A-2008-023232 | 2/2008 |
| JP | A-2008-228890 | 10/2008 |
| JP | A-2008-237571 | 10/2008 |
| JP | A-2009-022482 | 2/2009 |
| JP | A-2010-012037 | 1/2010 |

* cited by examiner

BODY FAT MEASUREMENT DEVICE

TECHNICAL FIELD

The present invention relates to body fat measurement devices configured so as to be capable of calculating the body fat mass of a measurement subject by measuring a body impedance, and particularly relates to body fat measurement devices configured so as to be capable of easily measuring a visceral fat mass and/or a subcutaneous fat mass in households or the like.

BACKGROUND ART

In recent years, fat mass is gaining attention as an indicator used to determine the health of a measurement subject. In particular, visceral fat mass is gaining attention as an indicator for determining whether or not a person is suffering from central obesity. Central obesity is said to bring about lifestyle-related diseases that can easily lead to artery hardening, such as diabetes, hypertension, and hyperlipidemia, and the stated indicators hold promise in terms of preventing such diseases. "Visceral fat" refers to fat that accumulates around the internal organs on the inner side of the abdominal muscles and the back muscles, and is distinct from the subcutaneous fat that is located toward the surface of the trunk area. It is typical to employ the area occupied by visceral fat in a cross-section of the trunk area that corresponds to the navel (referred to as a "visceral fat cross-sectional area" hereinafter) as an indicator of the visceral fat mass.

Normally, visceral fat mass is measured by analyzing images obtained through X-ray computed tomography (CT), magnetic resonance imaging (MRI), or the like. In such image analysis, the visceral fat cross-sectional area is calculated geometrically from a tomographic image of the trunk area obtained by using X-ray CT, MRI, or the like. However, it is necessary to use several pieces of large equipment installed in a medical facility, such as X-ray CT, MRI, or other machines, in order to make use of such a measurement method; thus it is extremely difficult to measure visceral fat mass on a daily basis through such a measurement method. X-ray CT also poses the problem of exposure to radiation, and thus cannot necessarily be called a desirable measurement method.

A body impedance technique is being considered as an alternative to these measurement methods. For example, JP 2002-369806A discloses a body fat measurement device configured having electrodes provided on the inner circumferential surface of a belt member, where the belt member is wrapped around and anchored to the trunk area of a measurement subject so that the electrodes are placed in contact with the trunk area; a body impedance is measured using the electrodes that have been placed in contact with the trunk area, and body fat mass, such as visceral fat mass and subcutaneous fat mass, can then be calculated based on the measured body impedance.

Meanwhile, to make it possible to measure the visceral fat mass, subcutaneous fat mass, and so on with a high degree of accuracy using the stated body impedance, it is necessary to take actual measurements of the measurement subject's body build, such as the circumferential length of the trunk area, the trunk area width, and the trunk area depth, and use the measurements in computational processes for calculating the body fat mass. JP 2005-288023A, JP 2008-23232A, JP 2008-237571A, JP 2009-22482A, and so on have been disclosed as body fat measurement devices that operate from such a standpoint, by taking actual measurements of the measurement subject's trunk area width, trunk area depth, and so on during measurement and using those measurements in computational processes for calculating the body fat mass.

The stated JP 2005-288023A discloses a body fat measurement device configured so that a fitting unit that is fitted to a measurement subject's abdominal area is provided upon a pair of arm portions, which make contact with both sides of the measurement subject's trunk area (in other words, both flanks), so that the fitting unit is mobile; the trunk area width is measured by bringing the arm portions into contact with both flanks.

The stated JP 2008-23232A discloses a body fat measurement device configured so that a fitting unit that is fitted to a measurement subject's abdominal area is provided upon an arm portion, which makes contact with the measurement subject's back, so that the fitting unit is mobile; the trunk area depth is measured by bringing the arm portion into contact with the back.

The stated JP 2008-237571A discloses a body fat measurement device configured so that a trunk area width measurement unit disposed at a distance from the outside of both sides of a measurement subject's trunk area is separate from a fitting unit fitted to the measurement subject's abdominal area; the configuration is such that multiple non-contact range sensors are provided in the trunk area width measurement unit in order to take an actual measurement of the trunk area width.

Furthermore, the stated JP 2009-22482A discloses a body fat measurement device that, instead of placing electrodes in contact with a measurement subject's trunk area, provides foot electrodes on a platform unit onto which the measurement subject steps; a trunk area width measurement unit disposed at a distance from the outside of both sides of the measurement subject's trunk area is supported on a support column portion that extends upward from the stated platform unit while the measurement subject stands on the platform unit, and multiple non-contact range sensors are provided in the trunk area width measurement unit so as to take an actual measurement of the trunk area width.

In addition, although not discussing a specific device configuration, JP 2008-228890A mentions being able to accurately measure visceral fat mass and subcutaneous fat mass by placing electrodes in contact with the back of a measurement subject's trunk area (that is, the back) without placing electrodes in contact with the measurement subject's abdominal area and placing electrodes in contact with the hands and feet of the measurement subject, measuring the body impedance, and calculating the visceral fat mass and the subcutaneous fat mass based on the measured body impedance. One of the reasons for this is that the subcutaneous fat that accumulates on the abdominal area side is relatively thinner than the subcutaneous fat that accumulates on the back area side, and thus if the electrodes are placed in contact with the abdominal area, the current that is applied will flow through fat-free areas, which makes it easy for errors to occur.

CITATION LIST

Patent Literature

Patent Literature 1: JP 2002-369806A
Patent Literature 2: JP 2005-288023A
Patent Literature 3: JP 2008-23232A
Patent Literature 4: JP 2008-237571A
Patent Literature 5: JP 2009-22482A
Patent Literature 6: JP 2008-228890A

SUMMARY OF INVENTION

Technical Problem

Here, in order to realize a body fat measurement device configured to be capable of easily and accurately calculating visceral fat mass and subcutaneous fat mass at home using the body impedance technique, it is extremely important to meet the following two conditions: one, that the measurement can be performed easily through simple operations; and two, that the measurement subject can perform the measurement him/herself without help from an assistant or the like. In light of this, it is unrealistic for the measurement subject to lie face up or face down during the measurement; it is preferable to employ a configuration in which the measurement can be carried out from a standing or seated position. Therefore, employing a measurement position as disclosed in the stated JP 2002-369806A and JP 2009-22482A is favorable in terms of realizing a body fat measurement device for household use.

However, the body fat measurement device disclosed in the stated JP 2002-369806A places electrodes in contact with only the measurement subject's trunk area, and in that sense it is difficult to assert that body fat mass, such as visceral fat mass or the like, can be measured with a high degree of accuracy. As described above, in order to calculate body fat mass, such as visceral fat mass or the like, with a higher degree of accuracy, it is necessary to place electrodes in contact with the back, without placing electrodes in contact with the abdominal area, while also placing electrodes in contact with the hands and feet, as disclosed in the stated JP 2008-228890A; in this sense, it is necessary to place electrodes in contact with at least the measurement subject's lower limbs.

Meanwhile, when considering improvements to a body fat measurement device that enables visceral fat mass and subcutaneous fat mass to be calculated easily and accurately within a household using the body impedance technique, the ability to store the device compactly when not in use and avoid taking up space for storage is a very important condition. However, the body fat measurement device disclosed in the stated JP 2009-22482A is structured so that the platform unit and the trunk area width measurement unit are linked via the support column portion, which poses problems in that the device is extremely large and takes up a large amount of space for storage.

It is thus necessary to make some kind of improvement in order to realize a body fat measurement device that enables visceral fat mass and subcutaneous fat mass to be measured easily and accurately and that is highly usable within a household using the body impedance technique.

Having been achieved in order to solve the stated problems, it is an object of the present invention to provide a body fat measurement device capable of easily and accurately measuring body fat masses, such as visceral fat mass, and that is highly usable, even at home.

Solution to Problem

A body fat measurement device according to the present invention includes multiple electrodes, a body impedance measurement unit, a trunk area width detection unit, a body fat mass calculation unit, a trunk area width measurement unit, and a platform unit. The multiple electrodes are for making contact with predetermined areas of the surface of a measurement subject's body, and include at least lower limb electrodes for making contact with the surfaces of the measurement subject's lower limbs. The body impedance measurement unit is a unit that measures a body impedance of the measurement subject's body using the multiple electrodes. The trunk area width detection unit is a unit for measuring a trunk area width and a trunk area depth of the measurement subject. The body fat mass calculation unit is a unit that calculates a body fat mass based on the body impedance measured by the body impedance measurement unit and the trunk area width and trunk area depth detected by the trunk area width detection unit. The trunk area width measurement unit is a frame-shaped unit in which the trunk area width detection unit is provided and that is capable of being disposed so as to surround the measurement subject's trunk area. The platform unit is a unit for bringing the lower limb electrodes into contact with the soles of the measurement subject's feet when the measurement subject steps onto the platform unit. The trunk area width measurement unit can be attached to and removed from the platform unit so as to take on a stored state, in which the trunk area width measurement unit is stored in the platform unit, and an unstored state, in which the trunk area width measurement unit is removed from the platform unit.

In the body fat measurement device according to the present invention, it is preferable for at least part of the platform unit to be, during the stored state, contained within a hollow opening area of the trunk area width measurement unit into which the measurement subject's trunk area is inserted.

In the body fat measurement device according to the present invention, it is preferable for a support portion for supporting the trunk area width measurement unit to be provided so as to protrude from the peripheral surface of the platform unit.

In the body fat measurement device according to the present invention, it is preferable for a step section that contains at least part of the trunk area width measurement unit during the stored state to be provided in the peripheral edge of the top surface of the platform unit.

In the body fat measurement device according to the present invention, it is preferable for a recess section that contains at least part of the trunk area width measurement unit during the stored state to be provided in an area of the top surface of the platform unit that excludes the peripheral edge.

In the body fat measurement device according to the present invention, it is preferable for the trunk area width measurement unit to be contained within a containment chamber provided within the platform unit during the stored state.

In the body fat measurement device according to the present invention, it is preferable for the platform unit to be configured as a box member that can open and close.

In the body fat measurement device according to the present invention, it is preferable for the platform unit to be configured as a box member whose one side surface is open.

In the body fat measurement device according to the present invention, it is preferable for the platform unit to be configured as a box member provided with a drawer that can be pulled out and pushed in.

In the body fat measurement device according to the present invention, it is preferable for the trunk area width detection unit to be configured of a non-contact range sensor provided on at least one of a right side portion and a left side portion of the trunk area width measurement unit and a non-contact range sensor provided on a front portion of the trunk area width measurement unit.

In the body fat measurement device according to the present invention, the configuration may be such that at least one of a right side portion and a left side portion of the trunk area width measurement unit is able to move along the measurement subject's trunk area width direction during the fitted state, and at least one of a front portion and a rear portion of the trunk area width measurement unit is able to move along the measurement subject's trunk area depth direction during the fitted state, and in such a case, the trunk area width detection unit may be configured of a movement amount detection sensor that detects the amount by which the portion of the trunk area width measurement unit that can move has moved.

In the body fat measurement device according to the present invention, it is preferable for the trunk area width measurement unit to be stored, in the stored state, in the platform unit in a state in which the outer shape of the trunk area width measurement unit has been minimized.

In the body fat measurement device according to the present invention, it is preferable for the trunk area width measurement unit to be able to be broken down into multiple parts, and in such a case, for the trunk area width measurement unit to be, in the stored state, stored in the platform unit in the broken-down state.

In the body fat measurement device according to the present invention, it is preferable for the multiple electrodes to further include back area electrodes for making contact with the surface of a back area that corresponds to an area of the measurement subject's trunk area on the back side thereof, and in such a case, for the back area electrodes to be provided on the trunk area width measurement unit in an exposed state.

In addition, in such a case, it is preferable for the back area electrodes to be provided on a rear portion of the trunk area width measurement unit so that the contact surface of the back area electrodes faces forward toward the back area surface in the fitted state.

In the body fat measurement device according to the present invention, it is preferable for the multiple electrodes to further include upper limb electrodes for making contact with the surfaces of the measurement subject's upper limbs, and in such a case, for the upper limb electrodes to be provided on the surface of the trunk area width measurement unit in an exposed state. In addition, in such a case, it is preferable for the upper limb electrodes to be provided on at least one of a front portion, a right side portion, and a left side portion that exclude the rear portion of the trunk area width measurement unit.

In the body fat measurement device according to the present invention, it is preferable for the platform unit to include a body weight measurement unit that measures the weight of the measurement subject.

In the body fat measurement device according to the present invention, it is preferable for the body fat mass calculation unit to include at least one of a visceral fat mass calculation unit that calculates the visceral fat mass of the measurement subject and a subcutaneous fat mass calculation unit that calculates the subcutaneous fat mass of the measurement subject.

Advantageous Effects of Invention

According to the present invention, a highly usable body fat measurement device capable of measuring a body fat mass such as a visceral fat mass easily and accurately in a household or the like can be provided.

DESCRIPTION OF EMBODIMENTS

Figure 1A:
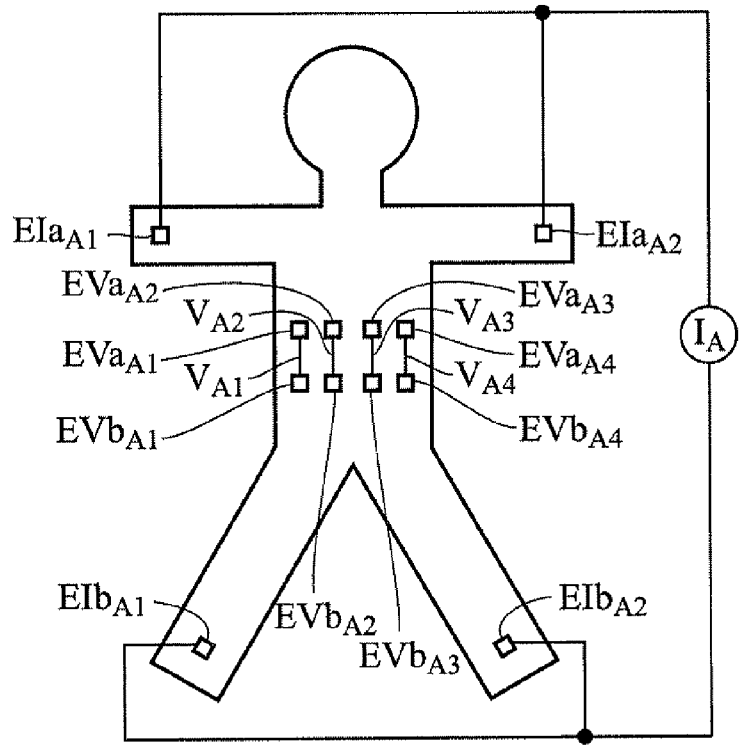
FIG. 1A is a diagram illustrating the fundamentals of measurement performed by a body fat measurement device according to a first embodiment of the present invention.

Hereinafter, embodiments of the present invention will be described in detail with reference to the drawings. Note that in the following embodiments, identical or corresponding elements are given the same reference numerals in the drawings, and individual descriptions thereof will not be repeated.

Before describing the various embodiments of the present invention, definitions will first be given for terms expressing parts of the body. "Trunk area" refers to the area excluding the head, neck, and four limbs, and corresponds to the trunk of the body. "Back area" refers to the area located on the back side of the stated trunk area, and corresponds to the area of the stated trunk area excluding the abdominal area side and the chest area side. "Back area surface" refers to the entire body surface of the back area, and indicates the surface of the trunk area that can be seen when a measurement subject is observed from the back side, Finally, "body axis" refers to an axis located along the direction in which the trunk area extends, or in other words, an axis extending in a direction approximately perpendicular to a side cross-section of the measurement subject's trunk area.

First Embodiment

Figure 1B:
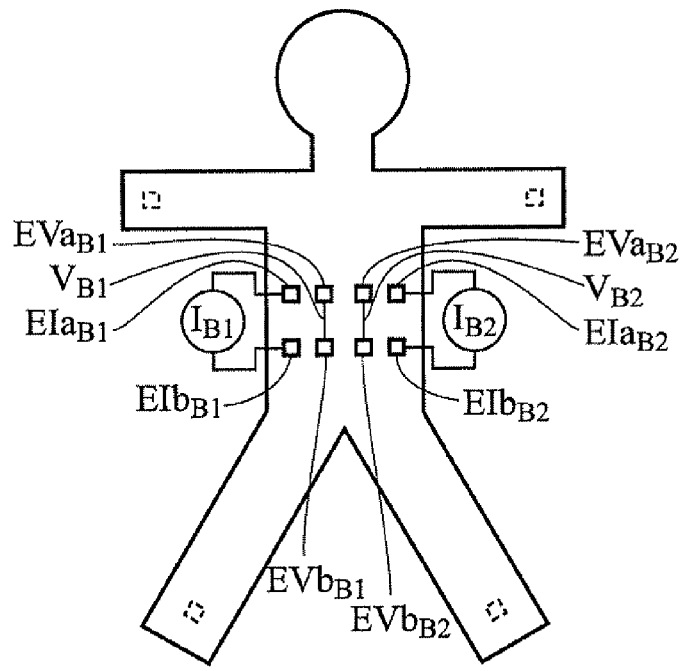
FIG. 1B is a diagram illustrating the fundamentals of measurement performed by the body fat measurement device according to the first embodiment of the present invention.

FIGS. 1A and 1B are diagrams illustrating the fundamentals of measurement performed by a body fat measurement device according to a first embodiment of the present invention. Here, FIG. 1A is a diagram illustrating the placement of electrodes when obtaining a body impedance for the entire trunk area, whereas FIG. 1B is a diagram illustrating the placement of electrodes when obtaining a body impedance for a surface layer area on the back area side of the trunk area. First, the fundamentals of measurement performed by the body fat measurement device according to the present embodiment will be described with reference to FIGS. 1A and 1B. Note that FIGS. 1A and 1B both illustrate the measurement subject from the back side thereof.

As shown in FIG. 1A, electrodes $EIa_{A1}$ and $EIa_{A2}$ are attached to the surface of the left hand of the measurement subject and the surface of the right hand of the measurement subject, respectively, in order to obtain the body impedance for the entire trunk area. Likewise, electrodes $EIb_{A1}$ and $EIb_{A2}$ are attached to the surface of the left foot of the measurement subject and the surface of the right foot of the measurement subject, respectively. Four pairs of electrodes are attached to the back area surface of the measurement subject, with each pair disposed so as to follow the body axis direction, and with the four pairs arranged in the widthwise direction of the trunk area. In other words, as shown in FIG. 1A, a total of eight electrodes, or electrodes $EVa_{A1}$, $EVb_{A1}$, $EVa_{A2}$, $EVb_{A2}$, $EVa_{A3}$, $EVb_{A3}$, $EVa_{A4}$, and $EVb_{A4}$, are attached to the back area surface of the measurement subject.

In this state, a constant current $I_A$ that passes through the trunk area is applied to the measurement subject using the electrodes $EIa_{A1}$, $EIa_{A2}$, $EIh_{A1}$, and $EIb_{A2}$ attached to both hands and both feet, respectively. While the constant current $I_A$ is applied, a potential difference $V_{A1}$ is detected using the pair of electrodes $EVa_{A1}$ and $EVb_{A1}$ attached to the back area surface, a potential difference $V_{A2}$ is detected using the pair of electrodes $EVa_{A2}$ and $EVb_{A2}$ attached to the back area surface, a potential difference $V_{A3}$ is detected using the pair of electrodes $EVa_{A3}$ and $EVb_{A3}$ attached to the back area surface, and a potential difference $V_{A4}$ is detected using the pair of electrodes $EVa_{A4}$ and $EVb_{A4}$ attached to the back area surface.

A body impedance Zt of the entire trunk area is calculated from the potential differences $V_{A1}$, $V_{A2}$, $V_{A3}$, and $V_{A4}$ detected in this manner. Note that if the body impedance Zt is found at this time by calculating the average value of the four stated potential differences $V_{A1}$, $V_{A2}$, $V_{A3}$, and $V_{A4}$, it is possible to reduce the influence of variations in the fat distribution within the trunk area.

In this state, the constant current $I_A$ is flowing between both hands and both feet, which are positioned at a distance from the trunk area, and thus almost all of the applied constant current $I_A$ passes through areas of low electrical resistance, or in other words, through areas aside from fat. Accordingly, the stated body impedance Zt calculated from the potential differences $V_{A1}$, $V_{A2}$, $V_{A3}$, and $V_{A4}$ measured using the constant current $I_A$ is greatly influenced by the amount of non-fat areas (internal organs, muscle, and bone) within the trunk area. Accordingly, the area occupied by non-fat areas (called a "non-fat cross-sectional area" hereinafter) Sa in the cross-section of the trunk area in an area corresponding to the location of the navel can be estimated based on the stated body impedance Zt.

Meanwhile, as shown in FIG. 1B, the four pairs of electrodes are attached to the back area surface of the measurement subject with each pair disposed so as to follow the body axis direction, and with the four pairs arranged in the widthwise direction of the trunk area, in order to obtain the body impedance of the surface layer area on the back area side of the trunk area. In other words, as shown in FIG. 1B, a total of eight electrodes, or electrodes $EIa_{A1}$, $EIb_{B1}$, $EVa_{B1}$, $EVb_{B1}$, $EVa_{B2}$, $EVb_{B2}$, $EIa_{B2}$, and $EIb_{B2}$, are attached to the back area surface of the measurement subject.

In this state, a constant current $I_{B1}$ that passes through the back area locally is applied to the measurement subject using the pair of electrodes $EIa_{B1}$ and $EIb_{B1}$, and a constant current $I_{B2}$ that passes through the back area locally is applied to the measurement subject using the pair of electrodes $EIa_{B2}$ and $EIb_{B2}$. While the constant currents $I_{B1}$ and $I_{B2}$ are applied, a potential difference $V_{B1}$ is detected using the pair of electrodes $EVa_{B1}$ and $EVb_{B1}$ attached to the back area surface, and a potential difference $V_{B2}$ is detected using the pair of electrodes $EVa_{B2}$ and $EVb_{B2}$ attached to the back area surface. Here, the current values of the two constant currents $I_{B1}$ and $I_{B2}$ applied to the measurement subject are set to the same value.

A body impedance Zs of the surface layer area on the back area side of the trunk area is calculated form the potential differences $V_{B1}$ and $V_{B2}$ calculated in this manner. Note that if the body impedance Zs is found at this time by calculating the average value of the two stated potential differences $V_{B1}$ and $V_{B2}$, it is possible to reduce the influence of variations in the fat distribution within the surface layer area in the back area of the trunk area. Note that potential differences can also be calculated in four locations by switching circuits so that the electrodes to which the current was applied serve as electrodes for detecting the potential differences and the electrodes that were detecting the potential differences serve as electrodes for current application. Doing so makes it possible to further reduce the influence of variations in the subcutaneous fat and so on.

In this state, the constant currents $I_{B1}$ and $I_{B2}$ are applied locally to the back area of the trunk area, and thus almost all of both the applied constant currents $I_{B1}$ and $I_{B2}$ pass through the surface layer area of the back area. Accordingly, the stated body impedance Zs calculated from the potential differences $V_{B1}$ and $V_{B2}$ measured using the constant currents $I_{B1}$ and $I_{B2}$ is greatly influenced by the subcutaneous fat mass. Accordingly, the subcutaneous fat cross-sectional area (called a "subcutaneous fat cross-sectional area" hereinafter) Sb in the cross-section of the trunk area including the location of the navel can be estimated based on the stated body impedance Zs.

Next, an example of a computation process for calculating a visceral fat mass using the stated body impedances Zt and Zs obtained in this manner will be described.

If the overall area of the cross-section of the trunk area at the area corresponding to the location of the navel (called a "trunk area cross-sectional area" hereinafter) is taken as St, a visceral fat cross-sectional area Sx can be calculated through the following Formula (1) using the trunk area cross-sectional area St, the non-fat cross-sectional area Sa, and the subcutaneous fat cross-sectional area Sb.

$$Sx = St - Sa - Sb \quad \text{Formula (1)}$$

Here, the trunk area cross-sectional area St can be calculated using the circumferential length of the trunk area (the so-called waist length), the width of the trunk area, the depth of the trunk area, and so on. For example, in the case where the trunk area cross-sectional area St is to be calculated from the width and depth of the trunk area, assuming that the width of the trunk area is taken as 2a and the depth of the trunk area is taken as 2b, and because the trunk area has a generally oval cross-sectional shape, the trunk area cross-sectional area St can be approximated through the following Formula (2).

$$St = \pi \times a \times b \quad \text{Formula (2)}$$

However, the trunk area cross-sectional area St approximated through the above Formula (2) is highly likely to contain a significant degree of error, and it is thus preferable to find a more accurate trunk area cross-sectional area St by multiplying that trunk area cross-sectional area St by a coefficient α for reducing error. This coefficient α is obtained, for example, by finding the optimum value for α that fulfills St'=α×π×a×b, from the relationship between the stated a and b and a trunk area cross-sectional area St' obtained from a sample of a large number of X-ray CT images.

Accordingly, the stated Formula (2) can approximate with a lower degree of error through the following Formula (3) by using the coefficient α.

$$St = \alpha \times \pi \times a \times b \quad \text{Formula (3)}$$

Note that it is preferable to optimize the coefficient α multiplied for correction as described above as appropriate in accordance with information such as the measurement subject's sex, age, height, weight, and so on (hereinafter, this information will be referred to collectively as "measurement subject information"). In other words, the trunk area cross-sectional area St can be approximated with a higher degree of accuracy by changing the value of the stated coefficient α in accordance with the measurement subject information.

As described above, the non-fat cross-sectional area Sa can be calculated based on the body impedance Zt of the entire trunk area. However, the non-fat cross-sectional area Sa cannot be accurately calculated using only the body impedance Zt of the entire trunk area. That is, the non-fat cross-sectional area Sa tends to be proportional to the size of the trunk area, and thus it is necessary to further convert the value obtained from the body impedance Zt in order to calculate the non-fat cross-sectional area Sa. Accordingly, the non-fat cross-sectional area Sa can be expressed through, for example, the following Formula (4).

$$Sa = \beta \times a \times (1/Zt) \quad \text{Formula (4)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, β represents a coefficient for converting the body impedance Zt of the entire trunk area into the non-fat cross-sectional area Sa, and an optimum value can be found, for example, based on a sample of a large number of X-ray CT images, in the same manner as when finding the coefficient α. In other words, the optimum value for β that fulfils Sa'=β×a×(1/Zt) can be found from the relationship between a non-fat cross-sectional area Sa' obtained from a sample of a large number of X-ray CT images, the body impedance Zt of the entire trunk area of the measurement subject imaged by the X-ray CT, and the stated a.

Note that it is preferable for the stated coefficient β to be optimized as appropriate in accordance with the measurement subject information, in the same manner as the coefficient α mentioned above. In other words, the non-fat cross-sectional area Sa can be approximated with a higher degree of accuracy by changing the value of the stated coefficient β in accordance with the measurement subject information.

Furthermore, as described above, the subcutaneous fat cross-sectional area Sb can be calculated based on the body impedance Zs of the surface layer area on the back area side of the trunk area. However, the subcutaneous fat cross-sectional area Sb cannot be accurately calculated using only the body impedance Zs of the surface layer area on the back area side of the trunk area. That is, the subcutaneous fat cross-sectional area Sb tends to be proportional to the size of the trunk area, and thus it is necessary to further convert the value obtained from the body impedance Zs in order to calculate the subcutaneous fat cross-sectional area Sb. Accordingly, the subcutaneous fat cross-sectional area Sb can be expressed through, for example, the following Formula (5).

$$Sb = \gamma \times a \times Zs \quad \text{Formula (5)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, γ represents a coefficient for converting the body impedance Zs of the surface layer area on the back area side of the trunk area into the subcutaneous fat cross-sectional area Sb, and an optimum value can be found, for example, based on a sample of a large number of X-ray CT images, in the same manner as when finding the coefficient α or the coefficient β. In other words, the optimum value for γ that fulfils Sb'=γ×a×Zs can be found from the relationship between a subcutaneous fat cross-sectional area Sb' obtained from a sample of a large number of X-ray CT images, the body impedance Zs of the surface layer area on the back area side of the trunk area of the measurement subject imaged by the X-ray CT, and the stated a.

Note that it is preferable for the stated coefficient γ to be optimized as appropriate in accordance with the measurement subject information, in the same manner as the coefficient α and the coefficient β mentioned above. In other words, the subcutaneous fat cross-sectional area Sb can be approximated with a higher degree of accuracy by changing the value of the stated coefficient γ in accordance with the measurement subject information.

As described thus far, in the body fat measurement device according to the present embodiment, the visceral fat cross-sectional area Sx is calculated based on the stated Formula (1) using the trunk area cross-sectional area St, the non-fat cross-sectional area Sa calculated based on the body impedance Zt of the entire trunk area, and the subcutaneous fat cross-sectional area Sb calculated based on the body impedance Zs of the surface layer area on the back area side of the trunk area; more specifically, the visceral fat cross-sectional area Sx is calculated based on the following Formula (6) by substituting the stated Formula (3) through Formula (5) in the stated Formula (1).

$$Sx = \alpha \times \pi \times a \times b - \beta \times a \times (1/Zt) - \gamma \times a \times Zs \quad \text{Formula (6)}$$

Figure 2:
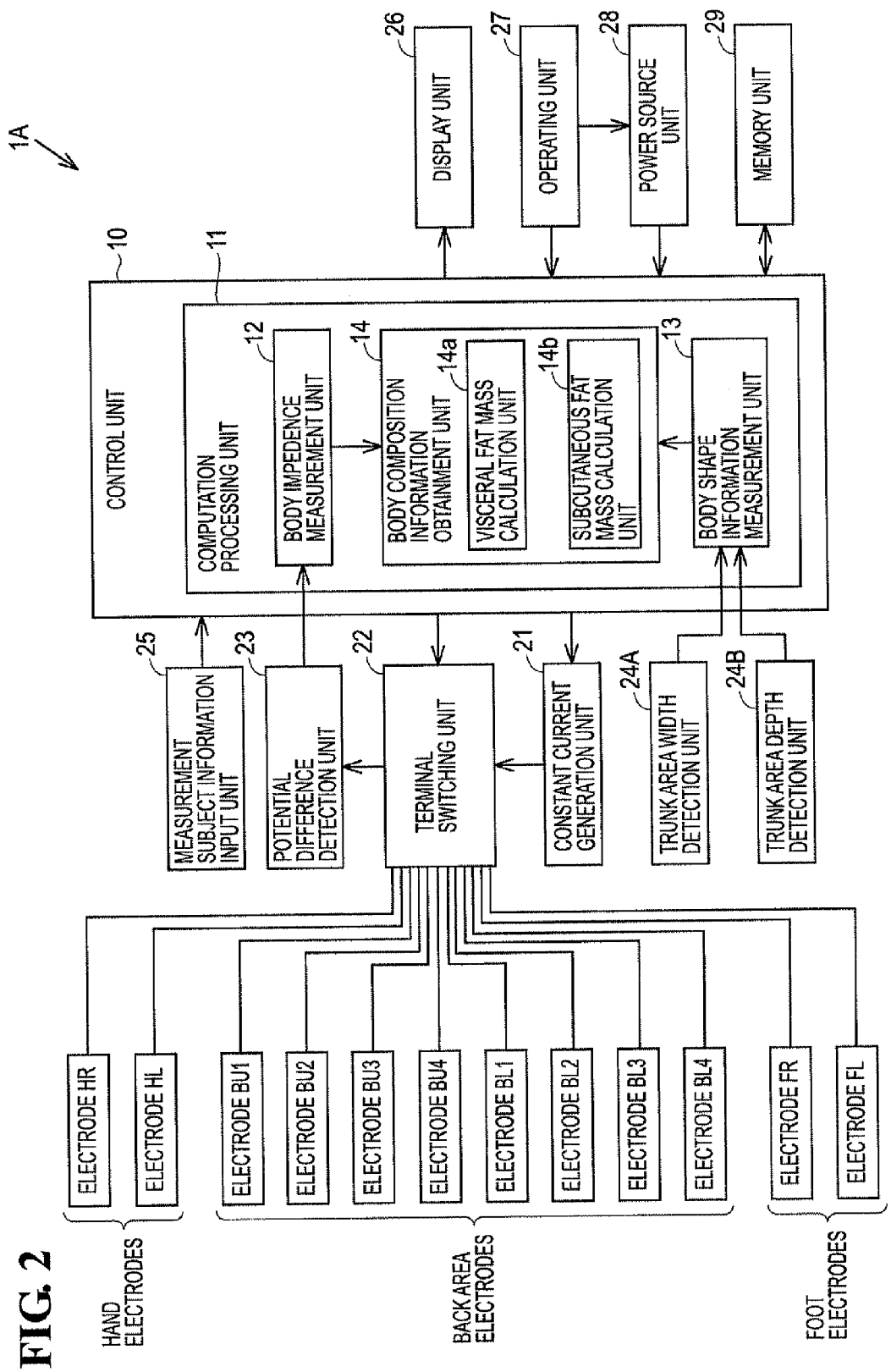
FIG. 2 is a diagram illustrating the functional block configuration of the body fat measurement device according to the first embodiment of the present invention.

FIG. 2 is a diagram illustrating the functional block configuration of the body fat measurement device according to the present embodiment. Next, the functional block configuration of the body fat measurement device according to the present embodiment will be described with reference to FIG. 2.

As shown in FIG. 2, a body fat measurement device 1A according to the present embodiment primarily includes: a control unit 10; a constant current generation unit 21; a terminal switching unit 22; a potential difference detection unit 23; a trunk area width detection unit 24A; a trunk area depth detection unit 24B; a measurement subject information input unit 25; a display unit 26; an operating unit 27; a power source unit 28; a memory unit 29; and multiple electrodes HR, HL, BU1-BU4, BL1-BL4, FR, and FL that are fitted to the body of the measurement subject. The control unit 10 includes a computation processing unit 11, and the computation processing unit 11 has a body impedance measurement unit 12, a body shape information measurement unit 13, and a body composition information obtainment unit 14.

The control unit 10 is configured of, for example, a CPU (Central Processor Unit), and is a unit for controlling the body fat measurement device 1A as a whole. Specifically, the control unit 10 outputs instructions to the various aforementioned functional blocks, accepts inputs of various types of information from the various aforementioned functional blocks, performs various types of computation processes based on the various types of information accepted, and so on. The various types of computation processes are carried out by the stated computation processing unit 11 provided in the control unit 10.

The aforementioned multiple electrodes include: hand electrodes HR and HL serving as upper limb electrodes placed in contact with surfaces of the upper limbs of the measurement subject; back area electrodes BU1-BU4 and BL1-BL4 placed in contact with the back area surface of the measurement subject; and foot electrodes FR and FL serving as lower limb electrodes placed in contact with surfaces of the lower limbs of the measurement subject. Of these, the hand electrodes HR and HL are placed in contact with the measurement subject's palms, whereas the foot electrodes FR and FL are placed in contact with the soles of the measurement subject's feet. Meanwhile, as shown in FIGS. 1A and 1B, the back area electrodes BU1-BU4 and BL1-BL4 are arranged in rows and placed in contact with the back area surface of the measurement subject, Note that the hand electrodes HR and HL, back area electrodes BU1-BU4 and BL1-BL4, and foot electrodes FR and FL are all electrically connected to the aforementioned terminal switching unit 22.

The terminal switching unit 22 is configured of, for example, a relay circuit; based on instructions inputted from the control unit 10, the terminal switching unit 22 electrically connects specific electrodes selected from the stated multiple electrodes to the constant current generation unit 21 and electrically connects specific electrodes selected from the stated multiple electrodes to the potential difference detection unit 23. Through this, the electrodes electrically connected to the constant current generation unit 21 by the terminal switching unit 22 function as constant current application electrodes, and the electrodes electrically connected to the potential difference detection unit 23 by the terminal switching unit 22 function as potential difference detection electrodes. In other words, by the terminal switching unit 22 operating based on instructions inputted from the control unit 10, the respective multiple electrodes HR, HL, BU1-BU4, BL1-BL4, FR, and FL function as the respective electrodes $EIa_{A1}$, $EIa_{A2}$, $EIb_{A1}$, $EIb_{A2}$, $EVa_{A1}$, $EVb_{A1}$, $EVa_{A2}$, $EVb_{A2}$, $EVa_{A3}$, $EVb_{A3}$, $EVa_{A4}$, and $EVb_{A4}$ shown in FIG. 1A and the respective electrodes $EIa_{B1}$, $EVb_{B1}$, $EVb_{B1}$, $EVa_{B2}$, $EVb_{B2}$, $EIa_{B2}$, and $EIb_{B2}$ shown in FIG. 1B.

The constant current generation unit 21 generates a constant current based on an instruction inputted from the control unit 10, and supplies the generated constant current to the stated constant current application electrodes via the terminal switching unit 22. A high-frequency current (for example, 50 kHz, 500 μA) that can be used effectively for measuring body composition information is selected as the constant current generated by the constant current generation unit 21. Through this, the constant current can be applied to the measurement subject via the constant current application electrodes.

The potential difference detection unit 23 detects a potential difference between the electrodes electrically connected to the potential difference detection unit 23 by the terminal switching unit 22 (that is, the potential difference detection electrodes), and outputs the detected potential difference to the control unit 10. Through this, the potential difference between the potential difference detection electrodes is detected in a state in which the aforementioned constant current is applied to the measurement subject.

The trunk area width detection unit 24A is a detection unit for measuring the width of the measurement subject's trunk area without making contact therewith, and is configured of, for example, a range sensor such as an optical sensor. Meanwhile, the trunk area depth detection unit 24B3 is a detection unit for measuring the depth of the measurement subject's trunk area without making contact therewith, and is configured of, for example, a range sensor such as an optical sensor. The trunk area width detection unit 24A and the trunk area depth detection unit 24B output signals based on the values detected to the body shape information measurement unit 13. In addition to the stated optical sensors, it should be noted that various types of non-contact range sensors that use ultrasound waves or electromagnetic waves (light of various wavelength ranges including laser light, visible light, and so on, radio waves, magnetism, electrical fields, and the like) can also be used as the trunk area width detection unit 24A and the trunk area depth detection unit 24B; contact-type range sensors can also be used.

The measurement subject information input unit 25 is a unit for obtaining information regarding the measurement subject used in computation processes carried out by the computation processing unit 11, and is configured of, for example, keys and the like that can be depressed by the measurement subject. Here, the measurement subject information includes at least one of the sex, age, height, weight, and so on of the measurement subject, as mentioned above, The measurement subject information input unit 25 accepts the input of measurement subject information, and outputs the accepted measurement subject information to the control unit 10. Note that the measurement subject information input unit 25 is not absolutely necessary in the configuration of the present invention, and whether or not to provide the measurement subject information input unit 25 can be determined based on whether or not it is necessary to use the measurement subject information in the computation processes performed by the computation processing unit 11. It is also possible to employ a configuration in which, instead of providing the trunk area width detection unit 24A and the trunk area depth detection unit 24B and actually measuring the width and depth of the trunk area, the circumferential length of the trunk area and so on are inputted via the measurement subject information input unit 25 and computations are carried out by a computation processing unit using that information.

The computation processing unit 11 includes the body impedance measurement unit 12, the body shape information measurement unit 13, and the body composition information obtainment unit 14, as mentioned above. Meanwhile, the body composition information obtainment unit 14 includes a visceral fat mass calculation unit 14a and a subcutaneous fat mass calculation unit 14b. The body impedance measurement unit 12 calculates the body impedance based on a signal inputted from the potential difference detection unit 23, and outputs that body impedance to the body composition information obtainment unit 14. The body shape information measurement unit 13 calculates the width and the depth of the measurement subject's trunk area based on the signals inputted from the trunk area width detection unit 24A and the trunk area depth detection unit 24B, and outputs the calculated information to the body composition information obtainment unit 14. The body composition information obtainment unit 14 calculates and obtains the body composition information based on the body impedance inputted from the body impedance measurement unit 12, the width and depth of the trunk area inputted from the body shape information measurement unit 13, and in some cases, the measurement subject information inputted from the measurement subject information input unit 25 as well. More specifically, the visceral fat mass calculation unit 14a calculates a visceral fat mass and the subcutaneous fat mass calculation unit 14b calculates a subcutaneous fat mass.

The display unit 26 is configured of, for example, an LCD (Liquid Crystal Display) or the like, and displays the body composition information calculated by the body composition information obtainment unit 14 as mentioned above. More specifically, the visceral fat mass calculated by the visceral fat mass calculation unit 14a and the subcutaneous fat mass calculated by the subcutaneous fat mass calculation unit 14b are displayed in the display unit 26 based on signals outputted from the control unit 10. Here, with the body fat measurement device 1A according to the present embodiment, the visceral fat mass is displayed as, for example, the visceral fat cross-sectional area, and the subcutaneous fat mass is displayed as, for example, the subcutaneous fat cross-sectional area.

The operating unit 27 is a unit through which the measurement subject inputs commands to the body fat measurement device 1A, and is configured of, for example, buttons and the like that can be depressed by the measurement subject. Note that the operating unit 27 includes various types of operation buttons such as a power button, a measure button, and so on.

The power source unit 28 is a unit for supplying electrical power to the control unit 10, and uses an internal power source such as a battery, an external power source such as an AC outlet, or the like.

The memory unit 29 is configured of, for example, a random access memory (RAM) or a read-only memory (ROM), and is a unit for storing various types of data, programs, and the like for the body fat measurement device 1A. The memory unit 29 stores, for example, the aforementioned measurement subject information, the calculated body composition information, a body composition information measurement program for executing a body composition information measurement process (mentioned later), and so on.

Figure 3:
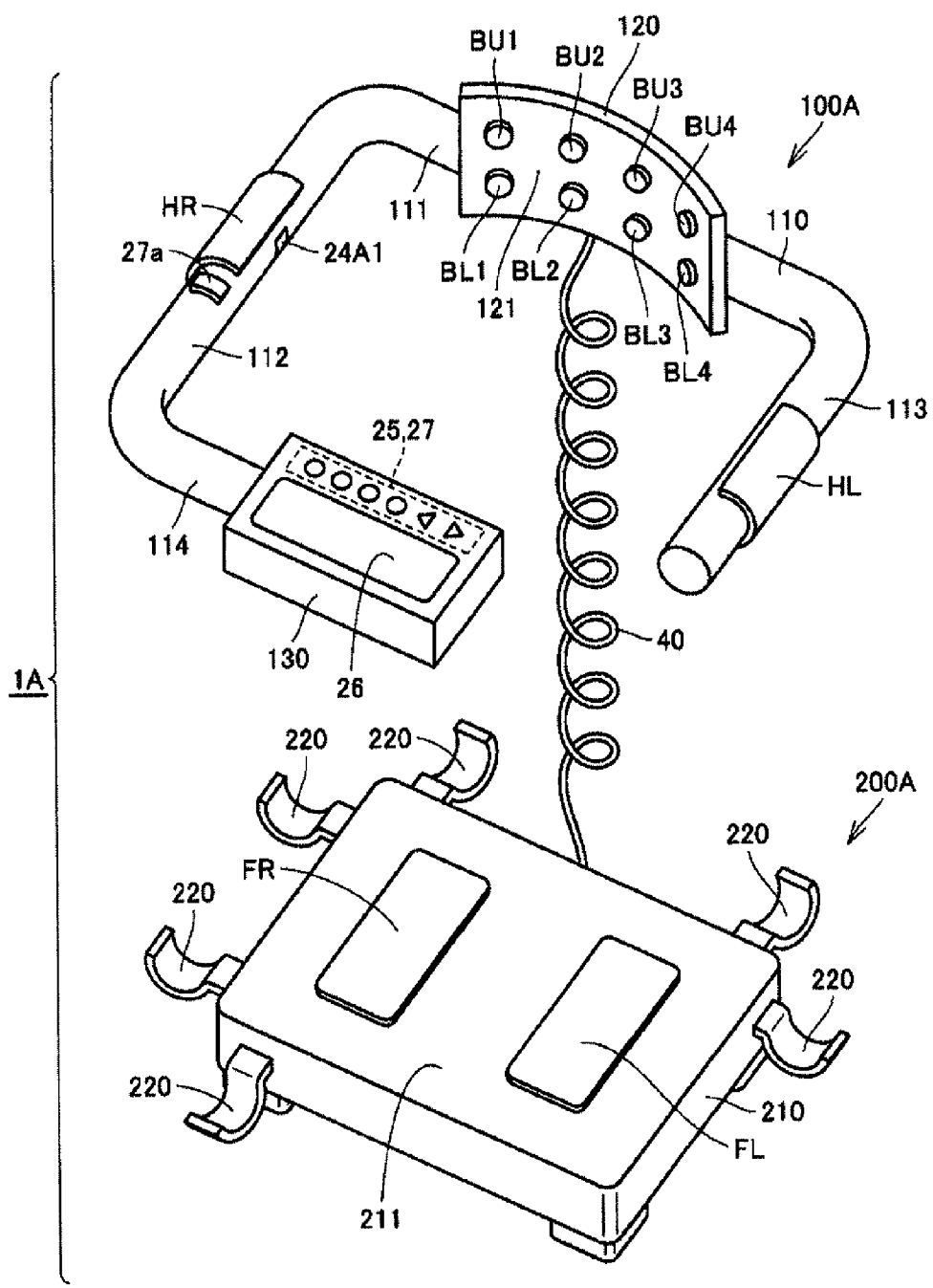
FIG. 3 is a perspective view illustrating the body fat measurement device according to the first embodiment of the present invention in an unstored state.
Figure 4:
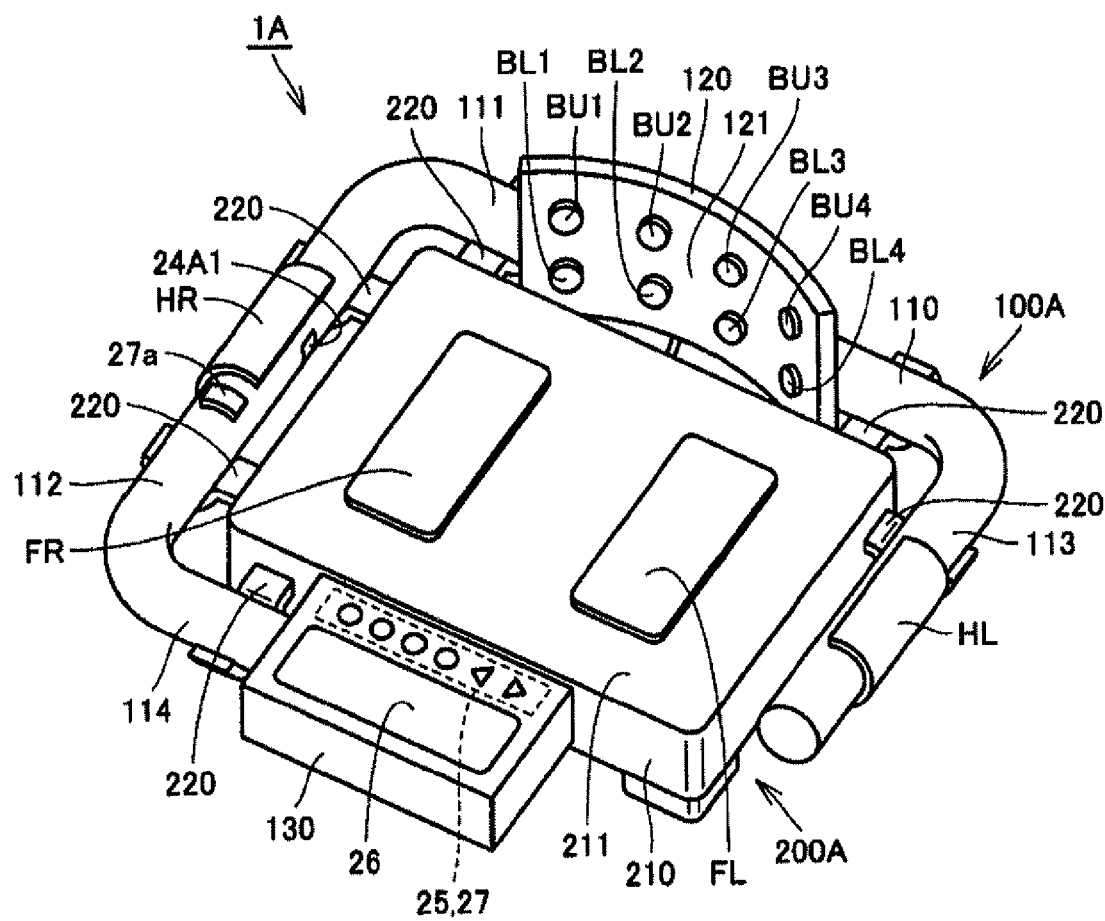
FIG. 4 is a perspective view illustrating the body fat measurement device according to the first embodiment of the present invention in a stored state.
Figure 5:
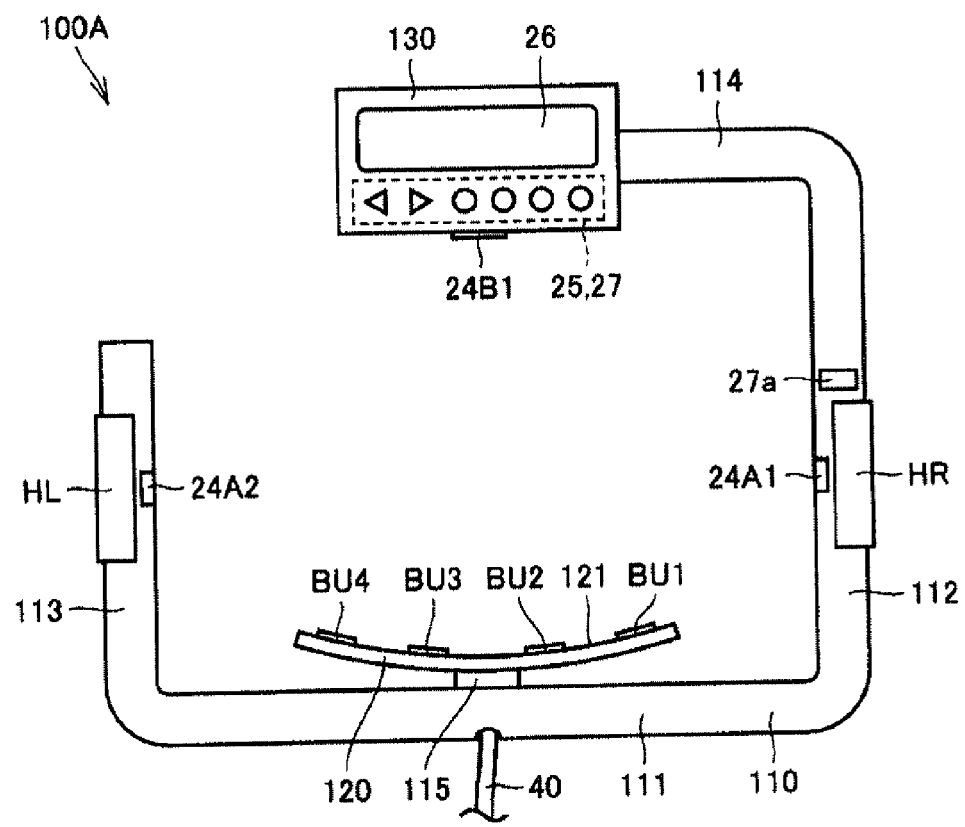
FIG. 5 is a top view of a fitting unit of the body fat measurement device according to the first embodiment of the present invention.

FIG. 3 is a perspective view illustrating the body fat measurement device according to the present embodiment in an unstored state, whereas FIG. 4 is a perspective view illustrating the body fat measurement device in a stored state. FIG. 5, meanwhile, is a top view of a fitting unit shown in FIGS. 3 and 4. Next, the structure of the body fat measurement device according to the present embodiment will be described in detail with reference to FIGS. 3 through 5.

As shown in FIGS. 3 and 4, the body fat measurement device 1A according to the present embodiment includes a fitting unit 100A, serving as a trunk area width measurement unit, and a platform unit 200A. The fitting unit 100A has a frame shape capable of being disposed so as to surround the trunk area of the measurement subject in a fitted state, which will be described later. Meanwhile, the platform unit 200A is shaped as a platform on which the measurement subject can stand. Note that the fitting unit 100A and the platform unit 200A are connected by a connection cable 40 that electrically connects electrical circuitry provided therein.

As shown in FIGS. 3 through 5, the fitting unit 100A includes: a frame member 110 that includes a rod-shaped rear frame portion 111, a rod-shaped right-side frame portion 112, a rod-shaped left-side frame portion 113, and a rod-shaped front frame portion 114; an electrode support member 120 attached to the rear frame portion 111 of the frame member 110; and a display unit portion 130 attached to the front frame portion 114 of the frame member 110.

The frame member 110 has a frame-shaped outer shape that is approximately rectangular when viewed from above, and has a hollow opening area into which the measurement subject can enter (in other words, into which the measurement subject can insert his/her trunk area). The hollow opening area is defined by the stated rear frame portion 111, right-side frame portion 112, left-side frame portion 113, and front frame portion 114. Note that the left-side frame portion 113 and the front frame portion 114 are not connected, and the aforementioned display unit portion 130 is attached to the end of the front frame portion 114 that is adjacent to the unconnected area.

The electrode support member 120 is disposed in approximately the center of the rear frame portion 111 of the frame member 110 so as to protrude inward. The electrode support member 120 is configured of a curved plate that is bent so that both ends thereof are positioned forward and the center thereof is positioned rearward. The aforementioned back area electrodes BU1-BU4 and BL1-BL4 are provided so as to be exposed on a front surface 121 of the electrode support member 120, and preferably, the back area electrodes BU1-BU4 and BL1-BL4 protrude slightly from the front surface 121 of the electrode support member 120. Here, the electrode support member 120 is positioned and attached on the front surface of the rear frame portion 111 so that surfaces of the back area electrodes BU1-BU4 and BL1-BL4 that make contact with the back area surface of the measurement subject face forward during the fitted state, which will be mentioned later.

Meanwhile, as shown in FIG. 5, the electrode support member 120 is attached to the rear frame portion 111 of the frame member 110 via a connection portion 115 including, for example, a ball joint. Through this, the electrode support member 120 is supported by the rear frame portion 111 in a pivotable state. Note that it is preferable for the direction of the pivoting to be limited so that the electrode support member 120 can pivot only to the left and right in the horizontal plane. Employing such a configuration makes it possible to bring the back area electrodes BU1-BU4 and BL1-BL4 provided on the front surface 121 of the electrode support member 120 into contact with the back area of the measurement subject with certainty and with an appropriate pressure during the fitted state, which will be mentioned later.

Alternatively, the connection portion 115 may be provided with an elastic member such as a spring, and configured so that the electrode support member 120 is elastically supported on the rear frame portion 111. Employing such a configuration makes it possible to bring the back area electrodes BU1-BU4 and BL1-BL4 provided on the front surface 121 of the electrode support member 120 into contact with the back area of the measurement subject with more certainty and with a more appropriate pressure during the fitted state, which will be mentioned later.

As shown in FIGS. 3 through 5, the aforementioned hand electrode HR is provided in approximately the center of the right-side frame portion 112 of the frame member 110. The hand electrode HR is positioned so as to be exposed on the surface of the right-side frame portion 112 of the frame member 110. Meanwhile, the area of the right-side frame portion 112 of the frame member 110 in which the hand electrode HR is provided is formed in a rod shape, so as to be capable of being gripped by the measurement subject's right hand. Here, it is preferable for the surface of the hand electrode HR that makes contact with the palm of the measurement subject's right hand to be disposed so as to mainly face outward from the frame member 110.

Meanwhile, an optical sensor, serving as the aforementioned trunk area width detection unit 24A, is embedded inside approximately the center of the right-side frame portion 112 of the frame member 110, and a detection window portion 24A1 is provided on the inner side of the right-side frame portion 112 in the area in which the optical sensor is embedded. The detection window portion 24A1 is configured of a member that allows light emitted from the optical sensor to pass through.

Furthermore, a measure button 27a is provided in a predetermined location of the right-side frame portion 112 of the frame member 110. Preferably, the measure button 27a is provided in a location adjacent to the hand electrode HR. As a result, it is not necessary for the measurement subject to move his/her right hand during measurement, which makes it possible to provide superior operability.

The aforementioned hand electrode HL is provided in approximately the center of the left-side frame portion 113 of the frame member 110. The hand electrode HL is positioned so as to be exposed on the surface of the left-side frame portion 113 of the frame member 110. Meanwhile, the area of the left-side frame portion 113 of the frame member 110 in which the hand electrode HL is provided is formed in a rod shape, so as to be capable of being gripped by the measurement subject's left hand. Here, it is preferable for the surface of the hand electrode HL that makes contact with the palm of the measurement subject's left hand to be disposed so as to mainly face outward from the frame member 110.

Meanwhile, as shown in FIG. 5, an optical sensor, serving as the aforementioned trunk area width detection unit 24A, is embedded inside approximately the center of the left-side frame portion 113 of the frame member 110, and a detection window portion 24A2 is provided on the inner side of the left-side frame portion 113 in the area in which the optical sensor is embedded. The detection window portion 24A2 is configured of a member that allows light emitted from the optical sensor to pass through.

As shown in FIGS. 3 through 5, the aforementioned display unit portion 130 is attached to the front frame portion 114 of the frame member 110. The display unit 26 is provided on the top surface of the display unit portion 130, and furthermore, the operating unit 27, excluding the measurement subject information input unit 25 and the measure button 27a, is provided on an area of the top surface of the display unit portion 130 that is adjacent to the display unit 26. Note that it is preferable for the display unit portion 130 to be located in front of the measurement subject during the fitted state, and for this reason, the display unit portion 130 is disposed forward from the aforementioned electrode support member 120 (that is, in approximately the center of the horizontal direction of the frame member 110).

Meanwhile, as shown in FIG. 5, an optical sensor, serving as the aforementioned trunk area depth detection unit 24B, is embedded inside the display unit portion 130, and a detection window portion 24B1 is provided on the rear surface side of the display unit portion 130 in the area in which the optical sensor is embedded. The detection window portion 24B1 is configured of a member that allows light emitted from the optical sensor to pass through.

Meanwhile, as shown in FIGS. 3 and 4, the platform unit 200A includes a box-shaped platform portion 210, and support portions 220 that protrude outward from predetermined locations on the front surface, the rear surface, the right-side surface, and the left-side surface of the platform portion 210 (in other words, from the peripheral sides of the platform portion 210).

The platform portion 210 has a top surface 211 onto which the measurement subject steps, and the aforementioned foot electrodes FR and FL are respectively provided in predetermined locations of the top surface 211. The foot electrodes FR and FL are positioned so as to be exposed on the top surface of the platform portion 210. Here, the configuration is such that the contact surfaces of the foot electrodes FR and FL that make contact with the sole of the measurement subject's right foot and the sole of the measurement subject's left foot are both facing upward.

As shown in FIG. 4, the support portions 220 are units for supporting and storing the fitting unit 100A during the stored state, and have shapes that are capable of accepting and supporting the rear frame portion 111, the right-side frame portion 112, the left-side frame portion 113, and the front frame portion 114, respectively, of the frame member 110. As shown in FIG. 4, during the stored state, where the fitting unit 100A is stored on the platform unit 200A, the frame member 110 of the fitting unit 100A is disposed so as to surround the platform portion 210 of the platform unit 200A, and thus part of the platform portion 210 is contained within the hollow opening area defined by the frame member 110.

Note that in the stored state, it is preferable for the configuration to be such that the connection cable 40 that connects the fitting unit 100A to the platform unit 200A is contained within the platform unit 200A. To achieve such a configuration, a reel member capable of taking up the connection cable 40 into the interior of the platform unit 200A may be provided.

The aforementioned control unit 10, constant current generation unit 21, terminal switching unit 22, potential difference detection unit 23, memory unit 29, and so on shown in FIG. 2 may be provided within the fitting unit 100A, or may be provided within the platform unit 200A. Furthermore, although the measurement subject information input unit 25, the display unit 26, and operating unit 27 are provided in the fitting unit 100A of the body fat measurement device 1A according to the present embodiment, those units may be provided within the platform unit 200A.

Figure 6:
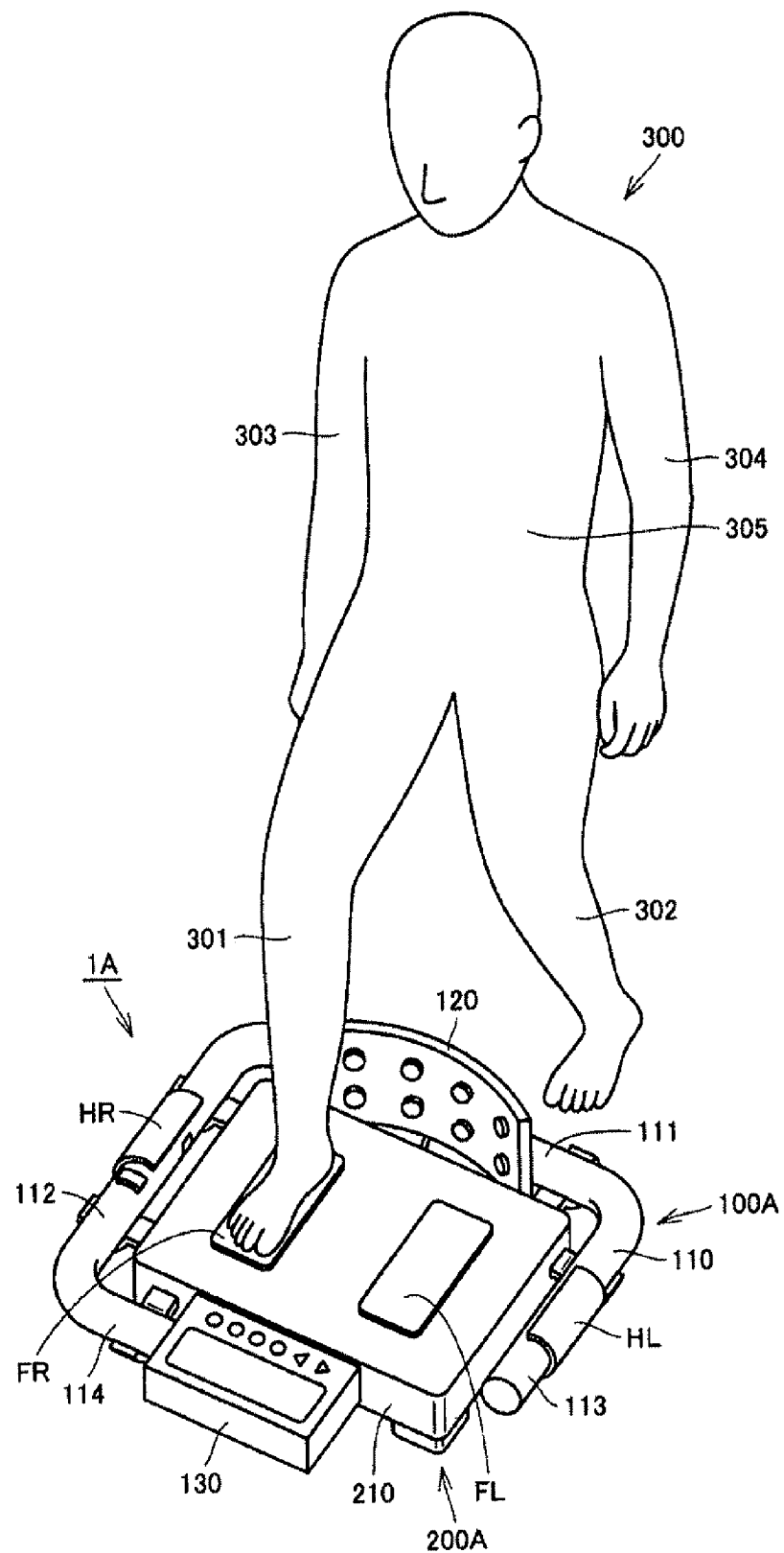
FIG. 6 is a diagram illustrating a procedure to be performed by a measurement subject when carrying out a measurement using the body fat measurement device according to the first embodiment of the present invention.
Figure 7:
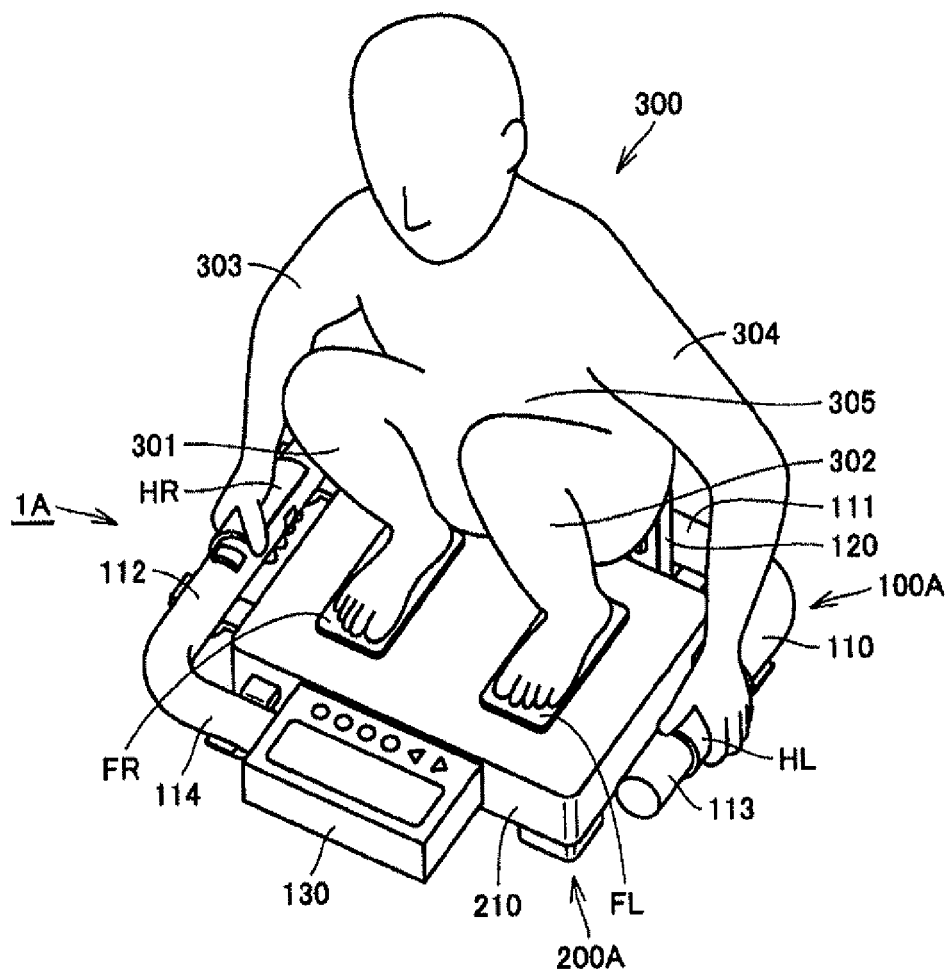
FIG. 7 is a diagram illustrating a procedure to be performed by a measurement subject when carrying out a measurement using the body fat measurement device according to the first embodiment of the present invention.
Figure 8:
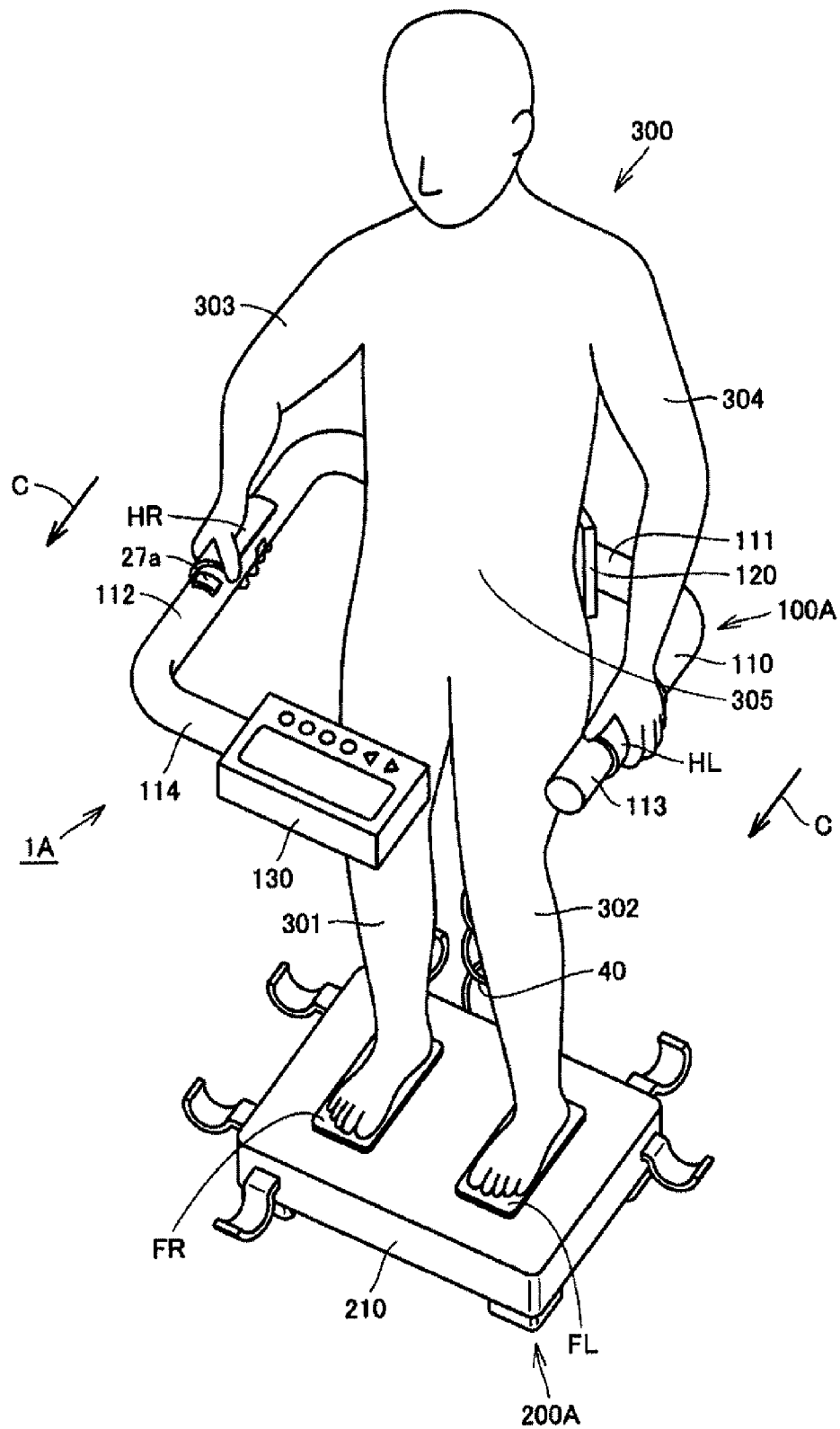
FIG. 8 is a diagram illustrating a procedure to be performed by a measurement subject when carrying out a measurement using the body fat measurement device according to the first embodiment of the present invention.
Figure 9:
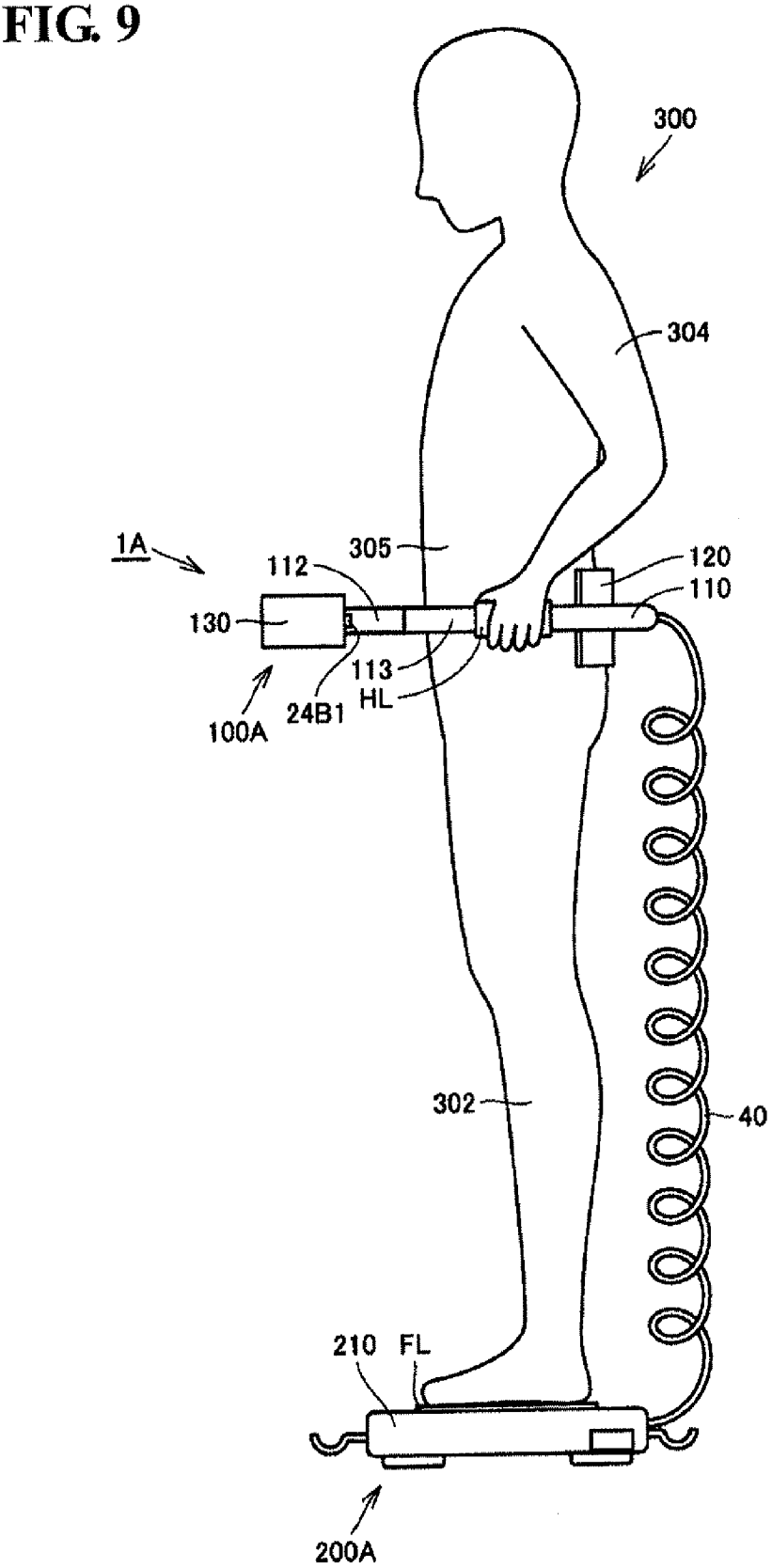
FIG. 9 is a diagram illustrating a fitted state of the fitting unit of the body fat measurement device according to the first embodiment of the present invention.
Figure 10:
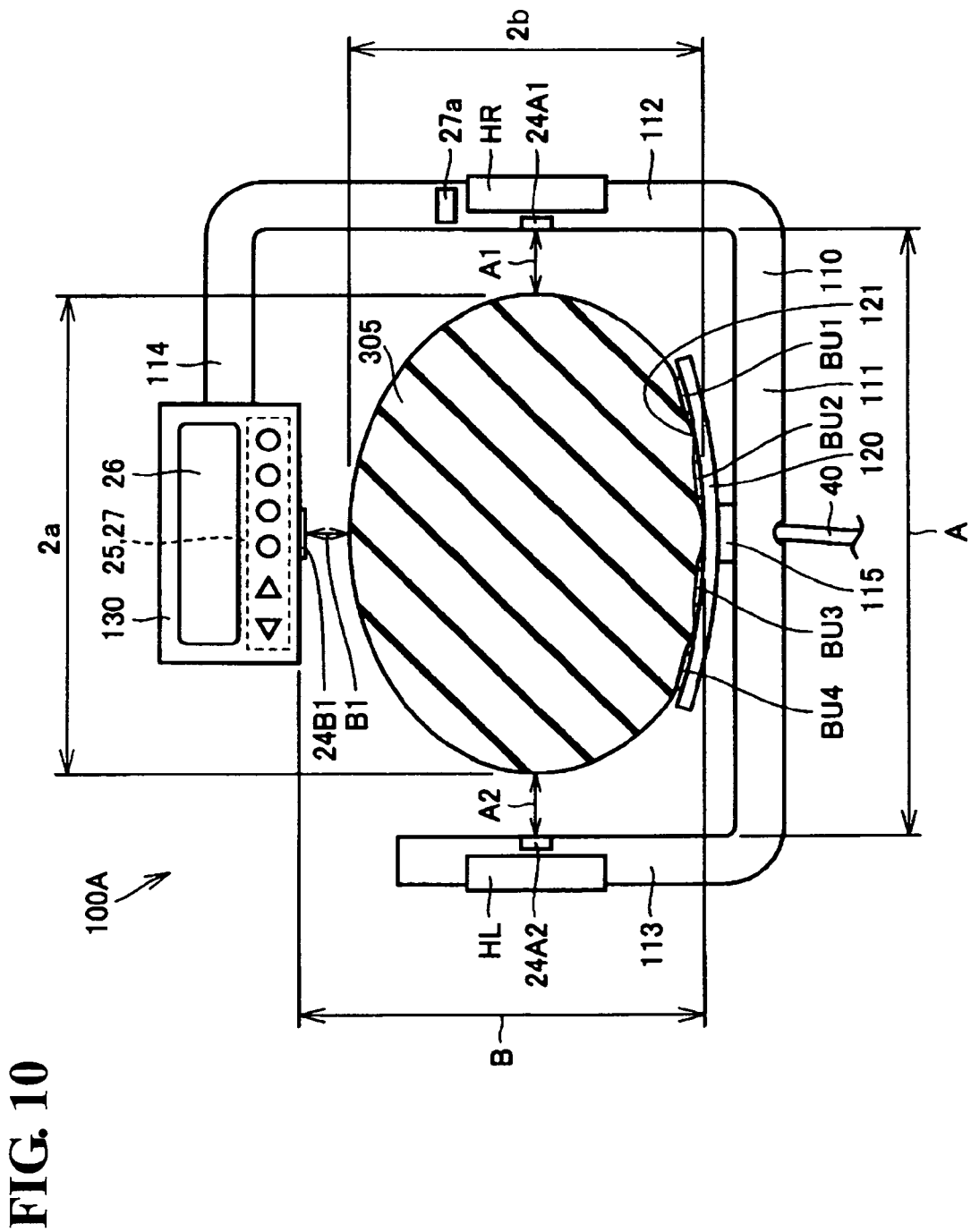
FIG. 10 is a diagram illustrating a fitted state of the fitting unit of the body fat measurement device according to the first embodiment of the present invention.

FIGS. 6 through 8 are diagrams illustrating a procedure to be performed by the measurement subject when carrying out a measurement using the body fat measurement device according to the present embodiment. Meanwhile, FIGS. 9 and 10 are diagrams illustrating the fitting unit of the body fat measurement device according to the present embodiment in the fitted state. Next, a procedure to be performed by the measurement subject and the fitted state of the fitting unit when carrying out measurement using the body fat measurement device according to the present embodiment will be described with reference to FIGS. 6 through 10.

As shown in FIG. 6, when measuring body fat mass using the body fat measurement device 1A according to the present embodiment, first, a measurement subject 300 steps onto the platform unit 200A of the body fat measurement device 1A in the stored state. At this time, the measurement subject 300 brings the sole of his/her right foot 301 into contact with the foot electrode FR provided on the platform unit 200A, and brings the sole of his/her left foot 302 into contact with the foot electrode FL provided on the platform unit 200A.

Next, as shown in FIG. 7, the measurement subject 300 bends his/her upper body and assumes a squatting position, and grips the right-side frame portion 112 of the fitting unit 100A with his/her right hand 303 and the left-side frame portion 113 of the fitting unit 100A with his/her left hand 304. At this time, the measurement subject 300 brings the palm of his/her right hand 303 into contact with the hand electrode HR provided in the fitting unit 100A, and brings the palm of his/her left hand 304 into contact with the hand electrode HL provided in the fitting unit 100A.

Next, as shown in FIG. 8, the measurement subject 300 straightens his/her upper body while gripping the fitting unit 100A, and assumes a standing position. As this time, the measurement subject 300 does not change his/her foot placement, keeping the sole of his/her right foot 301 in contact with the foot electrode FR and the sole of his/her left foot 302 in contact with the foot electrode FL. Here, the measurement subject 300 lifts the fitting unit 100A by straightening his/her body, and the trunk area 305 of the measurement subject 300 is then positioned in the hollow opening area of the fitting unit 100A, surrounded by the frame member 110. Note that the connection cable 40 is pulled from the platform unit 200A when the fitting unit 100A is lifted.

Next, the measurement subject 300 adjusts the position of the fitting unit 100A by moving the fitting unit 100A in the direction of an arrow C in FIG. 8 while continuing to grip the fitting unit 100A, so that the front surface 121 of the electrode support member 120 provided in the fitting unit 100A is pressed against the back area surface (more specifically, against the surface of his/her hips on the back side). Note that at this time, the measurement subject 300 takes care so that the frame member 110 of the fitting unit 100A is positioned horizontally.

As a result, the fitting unit 100A enters the fitted state shown in FIGS. 9 and 10, and the measurement of body fat mass can be started. Here, in order to start the measurement of the body fat mass, the measurement subject 300 may depress the measure button 27a using the thumb of his/her right hand 303. Although descriptions have been omitted above, the measurement subject 300 is required to press the power button at an appropriate timing. Although the timing at which the power button is pressed is not particularly limited, it is preferable for the power button to be pressed before the measurement subject 300 assumes a squatting position and grips the fitting unit 100A.

As shown in FIGS. 9 and 10, in the fitted state, where the fitting unit 100A is fitted to the measurement subject 300, the optical sensors serving as the trunk area width detection unit 24A and the optical sensor serving as the trunk area depth detection unit 24B are positioned around the trunk area 305 in a position including the location of the navel of the measurement subject 300. Accordingly, the light emitted from the pair of optical sensors serving as the trunk area width detection unit 24A can irradiate the right side surface of the trunk area 305 of the measurement subject 300 (in other words, the surface of the right flank) and the left side surface of the trunk area 305 (in other words, the surface of the left flank) through the detection window portions 24A1 and 24A2, and the light emitted from the optical sensor serving as the trunk area depth detection unit 24B can irradiate the front surface of the trunk area 305 of the measurement subject 300 (in other words, the vicinity of the location of the navel in the abdominal area) through the detection window portion 24B1.

Here, as shown in FIG. 10, a width $2a$ of the trunk area 305 of the measurement subject 300 can be calculated using a distance A1 (that is, the distance between the right-side frame portion 112 and the right side surface of the trunk area 305 of the measurement subject 300) and a distance A2 (that is, the distance between the left-side frame portion 113 and the left side surface of the trunk area 305 of the measurement subject 300) detected by the pair of optical sensors serving as the trunk area width detection unit 24A, along with a predetermined distance A (that is, the distance between the right-side frame portion 112 and the left-side frame portion 113). Likewise, a depth $2b$ of the trunk area 305 of the measurement subject 300 can be calculated using a distance B1 detected by the optical sensor serving as the trunk area depth detection unit 24B (that is, the distance between the rear surface of the display unit portion 130 and the front surface of the trunk area 305 of the measurement subject 300) and a predetermined distance B (that is, the distance between the rear surface of the display unit portion 130 and the center of the front surface 121 of the electrode support member 120 in the horizontal direction).

Figure 11:
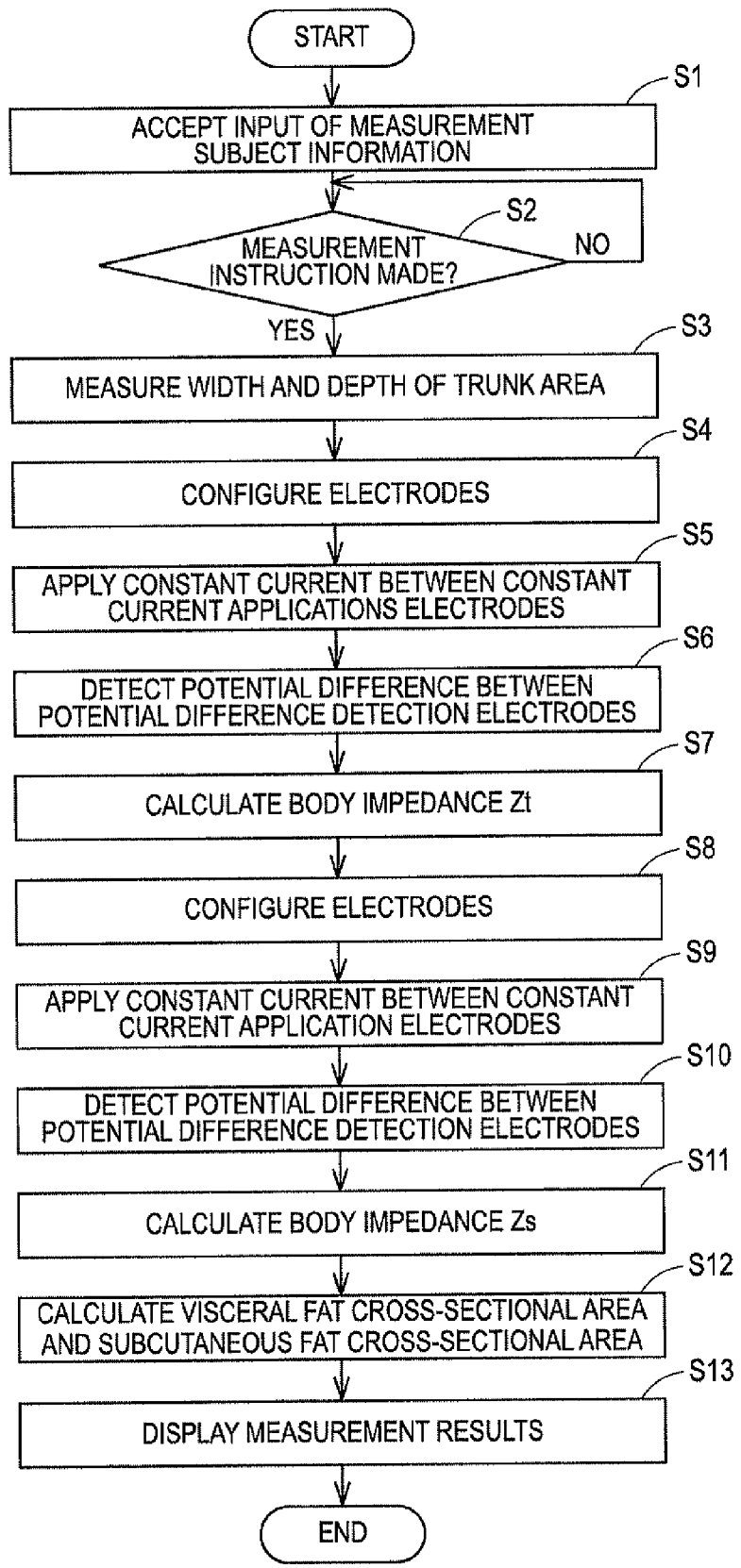
FIG. 11 is a flowchart illustrating a process performed by a control unit in the body fat measurement device according to the first embodiment of the present invention.

FIG. 11 is a flowchart illustrating a process performed by the control unit in the body fat measurement device according to the present embodiment. Next, a sequence of processes executed by the control unit of the body fat measurement device according to the present embodiment will be described with reference to FIG. 11. Note that the processes indicated in the flowchart in FIG. 11 are stored in the memory unit 29 in advance as a program, and a visceral fat cross-sectional area measurement process and a subcutaneous fat cross-sectional area measurement process are realized by the control unit 10 when the control unit 10 including the computation processing unit 11 reads out and executed that program.

As shown in FIG. 11, the control unit 10 first accepts an input of the measurement subject information (step S1). The accepted measurement subject information is temporarily saved in, for example, the memory unit 29.

Next, the control unit 10 determines whether or not there has been an instruction to start the measurement (step S2).

The control unit 10 stands by until there has been an instruction to start the measurement (NO in step S2), and advances to the next process in the case where an instruction to start the measurement has been detected (YES in step S2). Note that the instruction to start the measurement is made by the measurement subject depressing the measure button 27a.

Next, the control unit 10 measures the width and depth of the trunk area (step S3). Specifically, the control unit 10 obtains the width 2a and the depth 2b of the trunk area of the measurement subject using the body shape information measurement unit 13, based on signals inputted from the trunk area width detection unit 24A and the trunk area depth detection unit 24B. The obtained width 2a and depth 2b of the trunk area of the measurement subject are temporarily saved in the memory unit 29.

Next, the control unit 10 configures the electrodes (step S4). Specifically, the control unit 10 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1A.

Next, the control unit 10 applies a constant current between the constant current application electrodes (step S5). Specifically, the control unit 10 outputs an instruction to the constant current generation unit 21 for generating the constant current, and based on this, the constant current generation unit 21 applies the constant current $I_A$ generated between the constant current application electrodes as shown in FIG. 1A.

Next, the control unit 10 detects a potential difference between the potential difference detection electrodes (step S6). Specifically, the control unit 10 outputs an instruction to the potential difference detection unit 23 for detecting a potential difference, and based on this, the potential difference detection unit 23 detects the potential differences $V_{A1}$, $V_{A2}$, $V_{A3}$, and $V_{A4}$ between the potential difference detection electrodes shown in FIG. 1A, and outputs the detected potential differences to the body impedance measurement unit 12.

Next, the control unit 10 calculates the body impedance Zt (step S7). Specifically, the control unit 10 calculates the body impedance Zt using the body impedance measurement unit 12, based on a signal inputted from the potential difference detection unit 23. The calculated body impedance Zt is temporarily saved in the memory unit 29.

Next, the control unit 10 reconfigures the electrodes (step S8). Specifically, the control unit 10 outputs an instruction to the terminal switching unit 22 for switching the electrodes, and based on this, the terminal switching unit 22 configures the multiple electrodes HR, HL, BU1-BU4, BL1-BL4, FR, and FL to the configuration of the electrodes shown in FIG. 1B.

Next, the control unit 10 applies a constant current between the constant current application electrodes (step S9). Specifically, the control unit 10 outputs an instruction to the constant current generation unit 21 for generating the constant current, and based on this, the constant current generation unit 21 applies the constant currents $I_{B1}$ and $I_{B2}$ generated between the constant current application electrodes as shown in FIG. 1B.

Next, the control unit 10 detects a potential difference between the potential difference detection electrodes (step S10). Specifically, the control unit 10 outputs an instruction to the potential difference detection unit 23 for detecting a potential difference, and based on this, the potential difference detection unit 23 detects the potential differences $V_{B1}$ and $V_{B2}$ between the potential difference detection electrodes shown in FIG. 1B, and outputs the detected potential differences to the body impedance measurement unit 12.

Next, the control unit 10 calculates the body impedance Zs (step S11). Specifically, the control unit 10 calculates the body impedance Zs using the body impedance measurement unit 12, based on a signal inputted from the potential difference detection unit 23. The calculated body impedance Zs is temporarily saved in the memory unit 29.

Next, the control unit 10 calculates the visceral fat cross-sectional area and the subcutaneous fat cross-sectional area (step S12). Specifically, the control unit 10 calculates the visceral fat cross-sectional area Sx as the visceral fat mass using the visceral fat mass calculation unit 14a and calculates the subcutaneous fat cross-sectional area Sb as the subcutaneous fat mass using the subcutaneous fat mass calculation unit 14b, based on the width 2a and depth 2b of the trunk area detected in step S3, the body impedance Zt calculated in step S7, and the body impedance Zs calculated in step S11. Note that the calculated visceral fat cross-sectional area Sx and subcutaneous fat cross-sectional area Sb are temporarily saved in the memory unit 29.

Then, the control unit 10 displays the measurement results (step S13). Specifically, the control unit 10 outputs, to the display unit 26, an instruction to display the visceral fat cross-sectional area Sx and subcutaneous fat cross-sectional area Sb calculated in step S12, and based on this, the display unit 26 displays those measurement results.

Through this, the body fat measurement device 1A completes the visceral fat cross-sectional area measurement process and the subcutaneous fat cross-sectional area measurement process. Note that a typical value for the body impedance Zt is approximately 5Ω, whereas a typical value for the body impedance Zs is approximately 80Ω.

With the body fat measurement device 1A according to the present embodiment as described thus far, the configuration is such that the fitting unit 100A, in which are provided the trunk area width detection unit 24A for detecting the trunk area width and the trunk area depth detection unit 24B for detecting the trunk area depth, can be freely placed on and removed from the platform unit 200A, which brings the foot electrodes FR and FL into contact with the soles of the measurement subject's feet when the measurement subject steps thereon; thus the fitting unit 100A is stored on the platform unit 200A when in the stored state, and body fat mass such as the visceral fat mass can be measured in the unstored state, when the fitting unit 100A is removed from the platform unit 200A. Accordingly, the size of the device during storage can be greatly reduced, and thus a highly usable body fat measurement device that does not require a large storage space can be realized.

Furthermore, with the body fat measurement device according to the aforementioned present embodiment, in addition to the trunk area width detection unit 24A and the trunk area depth detection unit 24B, the back area electrodes BU1-BU4 and BL1-BL4 are provided in the fitting unit 100A in an exposed state and the hand electrodes HR and HL serving as the upper limb electrodes are provided in the fitting unit 100A in an exposed state. In other words, the trunk area width detection unit 24A, the trunk area depth detection unit 24B, the back area electrodes BU1-BU4 and BL1-BL4, and the hand electrodes HR and HL are provided so as to be integrated with the fitting unit 100A that is configured as a single unit.

Accordingly, by gripping the fitting unit 100A with the right hand and the left hand, the measurement subject can place the hand electrodes HR and HL in contact with the palm of his/her right hand and the palm of his/her left hand, respectively, and can place the back area electrodes BU1-BU4 and BL1-BL4 provided in the fitting unit 100A in contact with his/her back area surface by pressing the fitting unit 100A to the back area surface while gripping the fitting unit 100A with his/her right hand and left hand; furthermore, actual measurements of the trunk area width and the trunk area depth can be taken in this state. Accordingly, the operations required of the measurement subject when measuring the body fat mass can be simplified, and the body fat mass can be measured accurately and easily through a simple operation, and furthermore, the measurement subject can carry out the measurement him/herself without help from an assistant or the like.

Here, in the case where a configuration that places the electrodes in contact with the back area surface of the measurement subject is employed without employing the configuration of the body fat measurement device 1A according to the present embodiment as described above, it is difficult to maintain stable contact between the back area electrodes and the measurement subject's back area surface, and thus normally, it is necessary for the measurement subject to lie face up or face down in order to stabilize the contact. However, in the case where the device is configured in this manner, it is extremely difficult for the measurement subject to carry out the measurement by him/herself without help from an assistant or the like, and as a result, the body fat measurement device cannot be used in a household or the like.

However, as described above, with the body fat measurement device 1A according to the present embodiment, the trunk area width detection unit 24A, the trunk area depth detection unit 24B, the back area electrodes BU1-BU4 and BL1-BL4, and the hand electrodes HR and HL are provided so as to be integrated with the fitting unit 100A that is configured as a single unit, and thus the back area electrodes BU1-BU4 and BL1-BL4 can, with a simple operation, be brought into contact, in a stable manner, with the back area surface of the measurement subject who is standing up; in addition, the state of stable contact between the back area electrodes BU1-BU4 and BL1-BL4 and the measurement subject's back area surface can be maintained during the measurement operations, and furthermore, actual measurements can be taken of the trunk area width and the trunk area depth in such a state with a high degree of accuracy. Accordingly, with the body fat measurement device 1A according to the present embodiment, the operations required of the measurement subject when measuring the body fat mass can be simplified, and the body fat mass can be measured accurately and easily through a simple operation, and furthermore, the measurement subject can carry out the measurement him/herself without help from an assistant or the like.

Furthermore, with the body fat measurement device 1A according to the present embodiment, body fat mass such as the visceral fat mass, the subcutaneous fat mass, and so on can be measured while the back area electrodes BU1-BU4 and BL1-BL4 are placed in contact with the back area surface of the measurement subject, and thus instead of a current being locally applied to the abdominal area, where the subcutaneous fat is relatively thin, a current can be locally applied to the back area, where the subcutaneous fat is relatively thick; thus the body fat mass can be measured with a higher degree of accuracy.

Accordingly, the body fat measurement device 1A according to the present embodiment makes it possible to realize a body fat measurement device capable of measuring body fat mass, such as visceral fat mass and subcutaneous fat mass, easily and accurately and with high usability within a household or the like. Therefore, using the body fat measurement device 1A makes it possible to obtain such indicators for health management on a daily basis.

Second Embodiment

Figure 12:
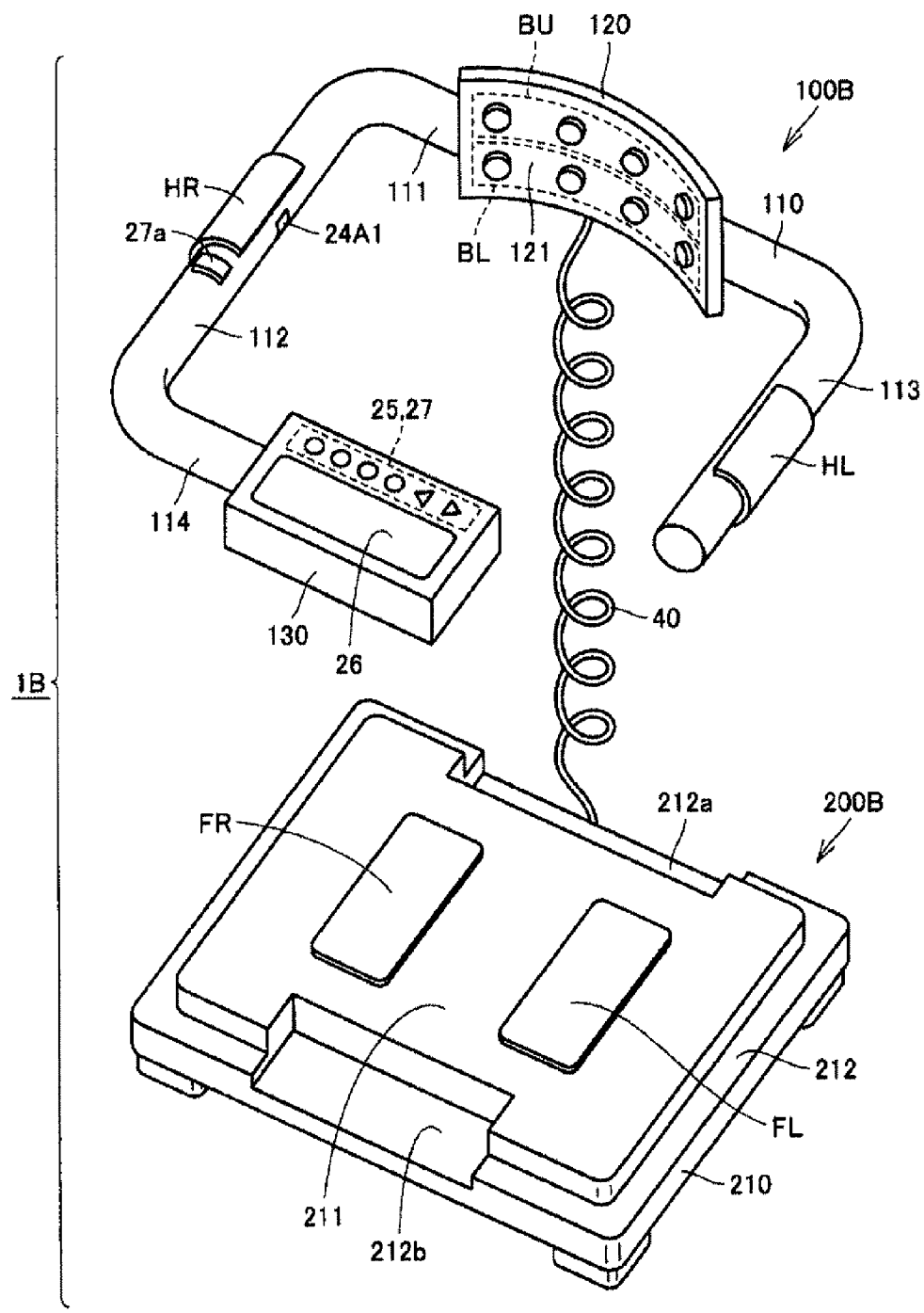
FIG. 12 is a perspective view illustrating a body fat measurement device according to a second embodiment of the present invention in an unstored state.
Figure 13:
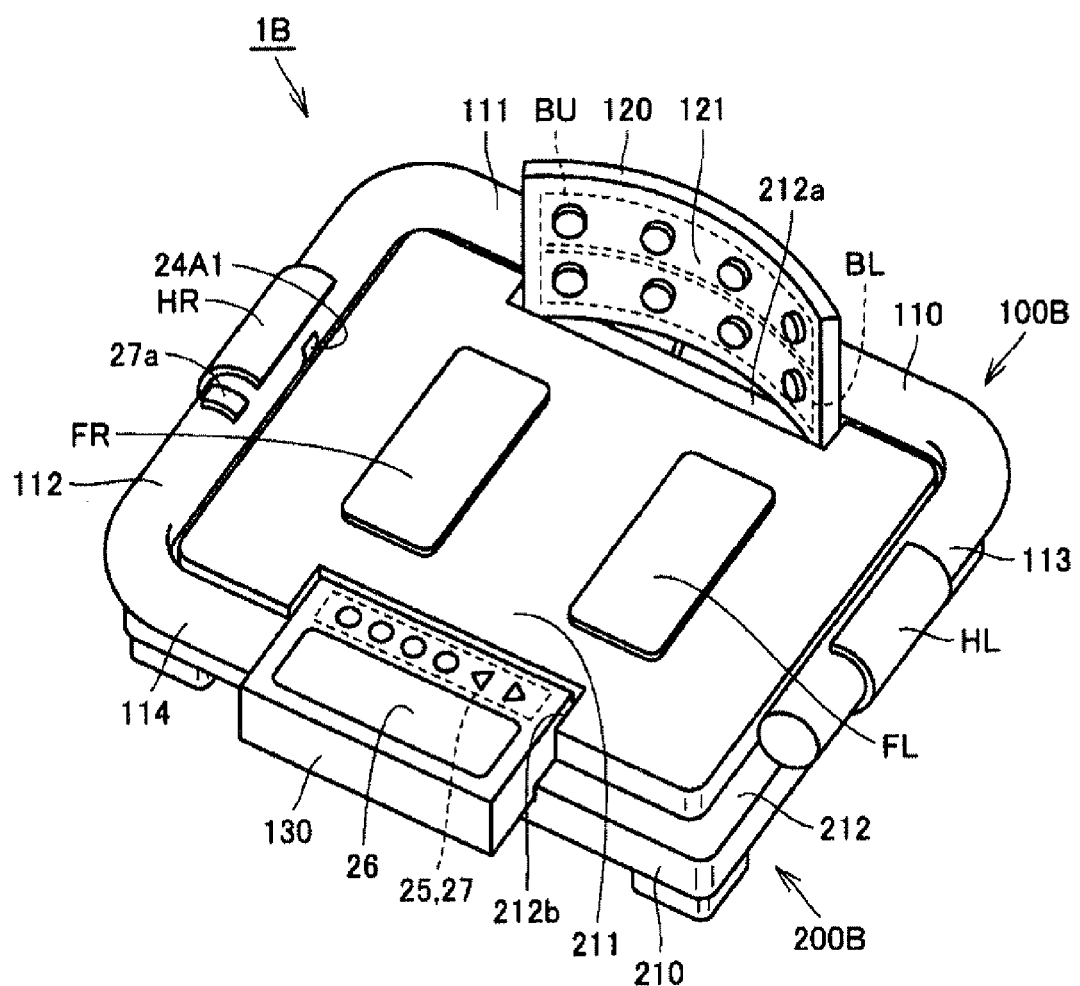
FIG. 13 is a perspective view illustrating the body fat measurement device according to the second embodiment of the present invention in a stored state.

FIG. 12 is a perspective view illustrating a body fat measurement device according to a second embodiment of the present invention in an unstored state, whereas FIG. 13 is a perspective view illustrating the body fat measurement device in a stored state. Next, the structure of the body fat measurement device according to the present embodiment will be described in detail with reference to FIGS. 12 and 13. Note that the fundamentals of the measurement performed by the body fat measurement device, the computation processes executed by the control unit, and so on according to the present embodiment are the same as those of the body fat measurement device according to the aforementioned first embodiment of the present invention.

As shown in FIGS. 12 and 13, a body fat measurement device 1B according to the present embodiment includes, like the body fat measurement device 1A according to the first embodiment of the present invention, a fitting unit 100B having a frame shape capable of being disposed so as to surround the trunk area of the measurement subject in a fitted state, and a platform unit 200B shaped as a platform on which the measurement subject can stand. Here, the body fat measurement device 1B according to the present embodiment differs from the body fat measurement device 1A according to the aforementioned first embodiment of the present invention in that there are no support portions positioned so as to protrude from the peripheral sides of the platform unit 200B, and instead, a step section 212 is provided by forming a step around the peripheral edge of the top surface 211 of the platform unit 200B.

As shown in FIG. 13, the step section 212 is a section for supporting and storing the fitting unit 100E during the stored state, and has a shape that is capable of accepting and supporting the rear frame portion 111, the right-side frame portion 112, the left-side frame portion 113, and the front frame portion 114, respectively, of the frame member 110. As shown in FIG. 13, during the stored state, where the fitting unit 100B is stored on the platform unit 200B, the frame member 110 of the fitting unit 100E is disposed so as to surround the platform portion 210 of the platform unit 200B, and thus part of the platform portion 210 is contained within the hollow opening area defined by the frame member 110.

Note that as shown in FIGS. 12 and 13, an electrode support member housing step section 212a is provided in a predetermined location of the part of the step section 212 that accepts and supports the rear frame portion 111 of the frame member 110, and during the stored state, the electrode support member 120 is accepted into and supported by the electrode support member housing step section 212a. Furthermore, a display unit portion housing step section 212b is provided in a predetermined location of the part of the step section 212 that accepts and supports the front frame portion 114 of the frame member 110, and during the stored state, the display unit portion 130 is accepted into and supported by the display unit portion housing step section 212b.

With the body fat measurement device 18 according to the present embodiment as described thus far, the same effects as those described in the aforementioned first embodiment of the present invention can be achieved.

Third Embodiment

Figure 14:
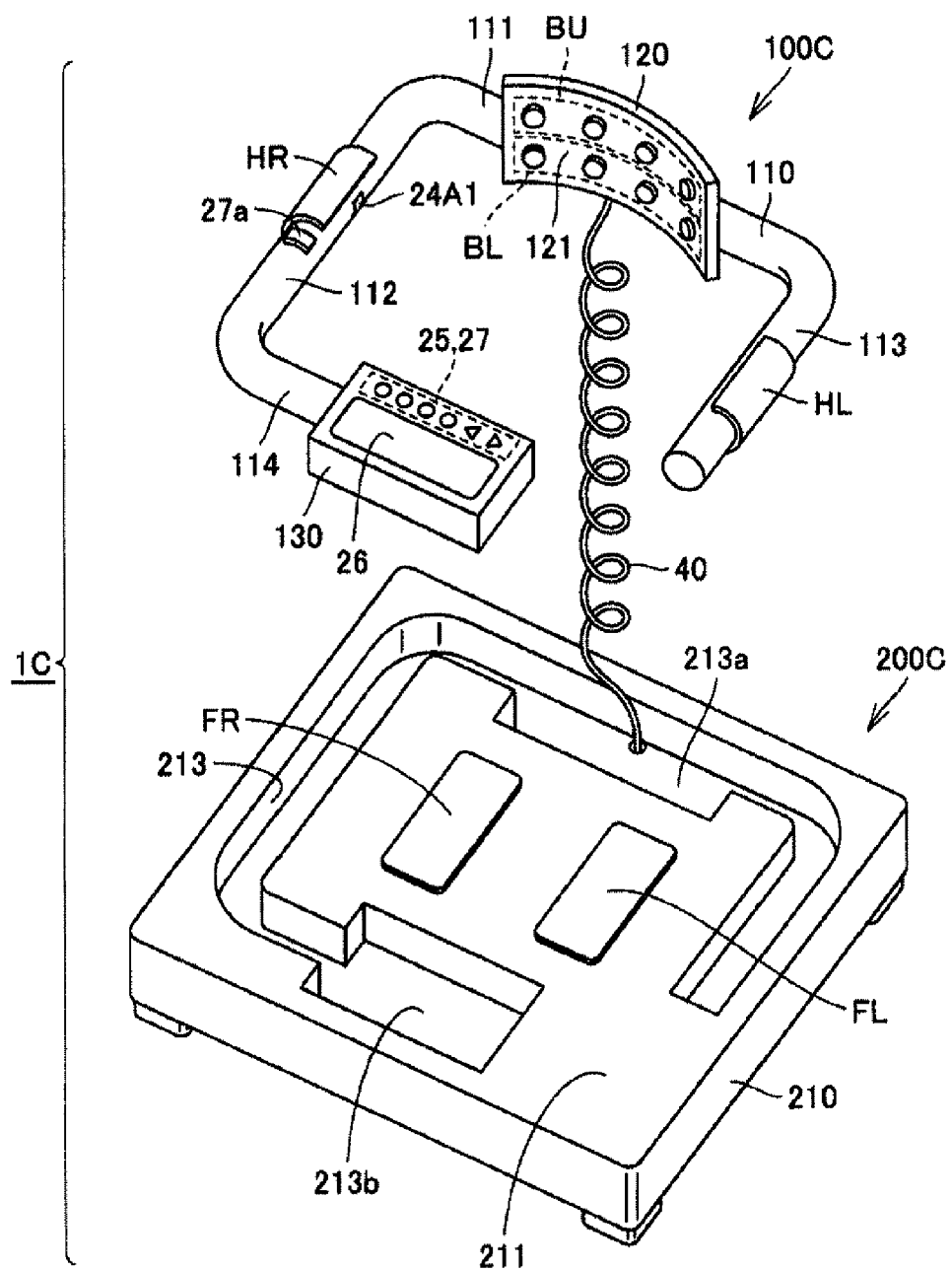
FIG. 14 is a perspective view illustrating a body fat measurement device according to a third embodiment of the present invention in an unstored state.
Figure 15:
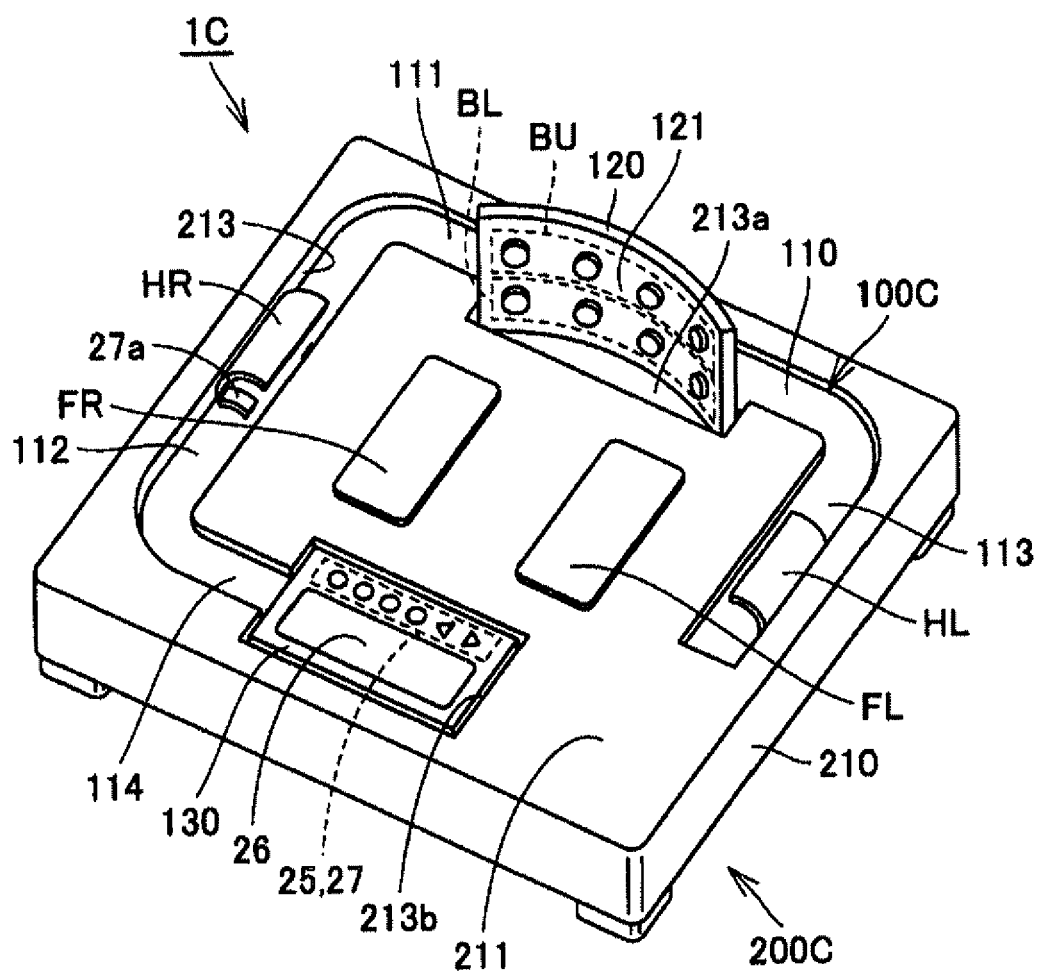
FIG. 15 is a perspective view illustrating the body fat measurement device according to the third embodiment of the present invention in a stored state.

FIG. 14 is a perspective view illustrating a body fat measurement device according to a third embodiment of the present invention in an unstored state, whereas FIG. 15 is a perspective view illustrating the body fat measurement device in a stored state. Next, the structure of the body fat measurement device according to the present embodiment will be described in detail with reference to FIGS. 14 and 15. Note that the fundamentals of the measurement performed by the body fat measurement device, the computation processes executed by the control unit, and so on according to the present embodiment are the same as those of the body fat measurement device according to the aforementioned first embodiment of the present invention.

As shown in FIGS. 14 and 15, a body fat measurement device 1C according to the present embodiment includes, like the body fat measurement device 1A according to the first embodiment of the present invention, a fitting unit 100C having a frame shape capable of being disposed so as to surround the trunk area of the measurement subject in a fitted state, and a platform unit 200C shaped as a platform on which the measurement subject can stand. Here, the body fat measurement device 1C according to the present embodiment differs from the body fat measurement device 1A according to the aforementioned first embodiment of the present invention in that there are no support portions positioned so as to protrude from the peripheral sides of the platform unit 200C, and instead, a recess section 213 is provided by forming a groove in areas of the top surface 211 of the platform unit 200C aside from the peripheral edges thereof.

As shown in FIG. 15, the recess section 213 is a section for supporting and storing the fitting unit 100C during the stored state, and has a shape that is capable of accepting and supporting the rear frame portion 111, the right-side frame portion 112, the left-side frame portion 113, and the front frame portion 114, respectively, of the frame member 110. As shown in FIG. 15, during the stored state, where the fitting unit 100C is stored on the platform unit 200C, the frame member 110 of the fitting unit 100C is disposed so as to surround the central area of the platform portion 210 of the platform unit 200C, and thus part of the platform portion 210 is contained within the hollow opening area defined by the frame member 110.

Note that as shown in FIGS. 14 and 15, an electrode support member housing recess section 213a is provided in a predetermined location of the part of the recess section 213 that accepts and supports the rear frame portion 111 of the frame member 110, and during the stored state, the electrode support member 120 is accepted into and supported by the electrode support member housing recess section 213a. Furthermore, a display unit portion housing recess section 213b is provided in a predetermined location of the part of the recess section 213 that accepts and supports the front frame portion 114 of the frame member 110, and during the stored state, the display unit portion 130 is accepted into and supported by the display unit portion housing recess section 213b.

With the body fat measurement device 1C according to the present embodiment as described thus far, the same effects as the effects described in the aforementioned first embodiment of the present invention can be achieved; furthermore, the configuration is such that a major part of the fitting unit 100C is housed within the platform unit 200C during the stored state, which prevents the fitting unit 100C from being damaged during storage.

Fourth Embodiment

Figure 16:
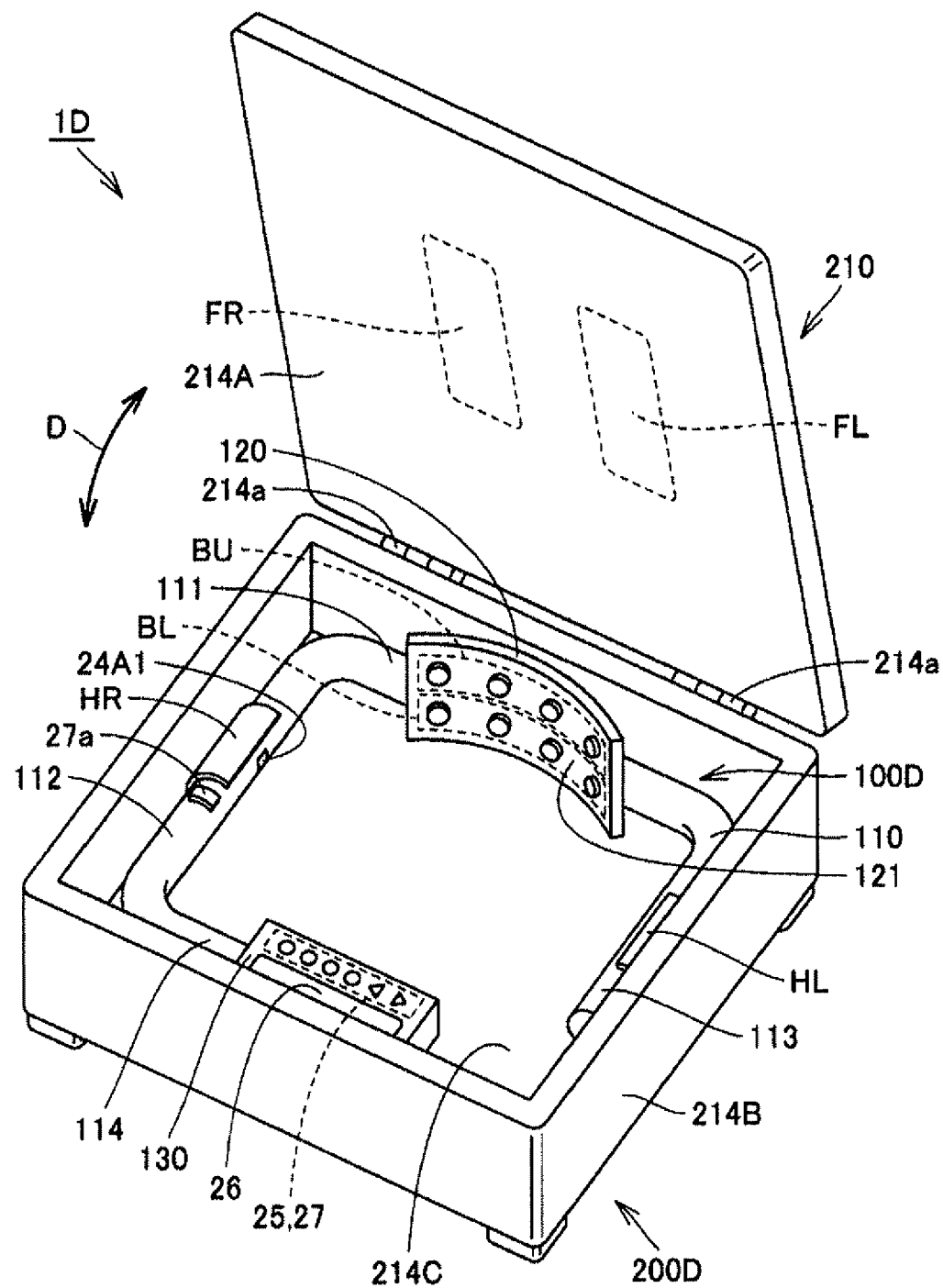
FIG. 16 is a perspective view illustrating a storage structure for a body fat measurement device according to a fourth embodiment of the present invention.

FIG. 16 is a perspective view illustrating a storage structure for a body fat measurement device according to a fourth embodiment of the present invention. Next, the structure of the body fat measurement device according to the present embodiment will be described in detail with reference to FIG. 16. Note that the fundamentals of the measurement performed by the body fat measurement device, the computation processes executed by the control unit, and so on according to the present embodiment are the same as those of the body fat measurement device according to the aforementioned first embodiment of the present invention.

As shown in FIG. 16, a body fat measurement device 1D according to the present embodiment includes, like the body fat measurement device IA according to the aforementioned first embodiment of the present invention, a fitting unit 100D having a frame shape capable of being disposed so as to surround the trunk area of the measurement subject in a fitted state, and a platform unit 200D shaped as a platform on which the measurement subject can stand. Here, the body fat measurement device 1D according to the present embodiment differs from the body fat measurement device 1A according to the aforementioned first embodiment of the present invention in that there are no support portions positioned so as to protrude from the peripheral sides of the platform unit 200D, and instead, the platform portion 210 of the platform unit 200D is configured as a box member capable of opening and closing.

Specifically, as shown in FIG. 16, the platform portion 210 of the platform unit 200D includes a cover plate portion 214A that configures the top surface of the platform portion 210, and an approximately square-shaped box portion 214B whose top surface is open. The cover plate portion 214A is attached to the box portion 214B by hinges 214a so as to be capable of pivoting in the direction indicated by the arrow D in FIG. 16, and the top surface opening of the stated box portion 214B is covered when in a closed state. A containment chamber 214C having a size that can contain the fitting unit 100D is provided within the box portion 214B. Note that the foot electrodes FR and FL serving as lower limb electrodes are provided on the top surface of the cover plate portion 214A.

As shown in FIG. 16, during the stored state, the fitting unit 100D is contained within the containment chamber 214C of the platform unit 200D, and thus the fitting unit 100D is stored within the platform unit 200D. In this state, the cover plate portion 214A can cover the stated top surface opening of the box portion 214B, which enables the fitting unit 100D to be stored in the platform unit 200D without being exposed to the exterior. Note that in order to facilitate the storage of the fitting unit 100D in the platform unit 200D, it is preferable for the configuration to be such that the connection cable 40 for connecting the fitting unit 100D and the platform unit 200D (see FIG. 3 and so on) is detachable from at least one of the fitting unit 100D and the platform unit 200D.

With the body fat measurement device 1D according to the present embodiment as described thus far, the same effects as the effects described in the aforementioned first embodiment of the present invention can be achieved; furthermore, the configuration is such that the fitting unit 100D is contained within the platform unit 200D during the stored state, which prevents the fitting unit 100D from being damaged during storage.

Fifth Embodiment

Figure 17:
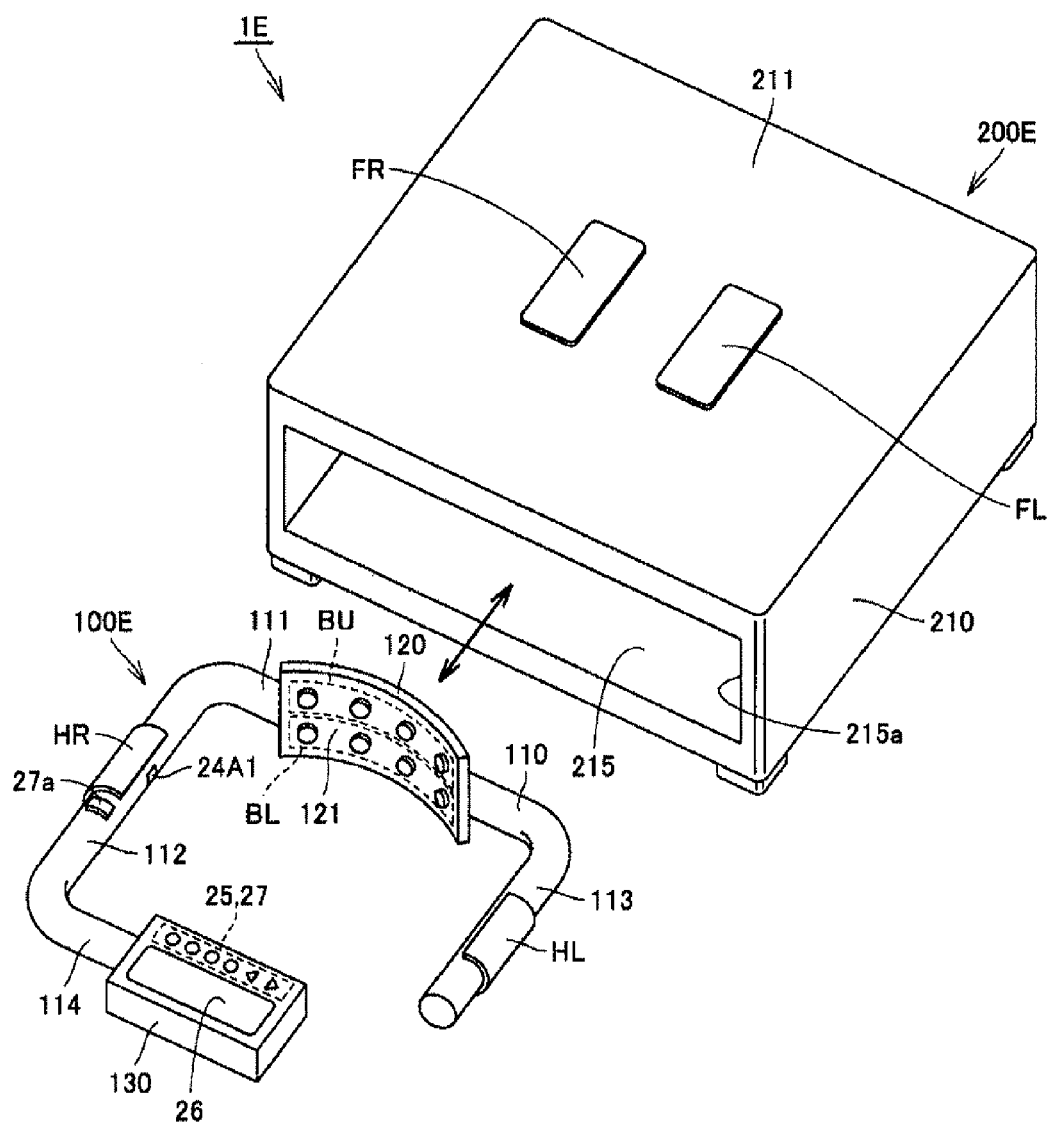
FIG. 17 is a perspective view illustrating a storage structure for a body fat measurement device according to a fifth embodiment of the present invention.

FIG. 17 is a perspective view illustrating a storage structure for a body fat measurement device according to a fifth embodiment of the present invention. Next, the structure of the body fat measurement device according to the present embodiment will be described in detail with reference to FIG. 17. Note that the fundamentals of the measurement performed by the body fat measurement device, the computation processes executed by the control unit, and so on according to the present embodiment are the same as those of the body fat measurement device according to the aforementioned first embodiment of the present invention.

As shown in FIG. 17, a body fat measurement device 1E according to the present embodiment includes, like the body fat measurement device 1A according to the aforementioned first embodiment of the present invention, a fitting unit 100E having a frame shape capable of being disposed so as to surround the trunk area of the measurement subject in a fitted state, and a platform unit 200E shaped as a platform on which the measurement subject can stand. Here, the body fat measurement device 1E according to the present embodiment differs from the body fat measurement device 1A according to the aforementioned first embodiment of the present invention in that there are no support portions positioned so as to protrude from the peripheral sides of the platform unit 200E, and instead, the platform portion 210 of the platform unit 200E is configured as a box member having one side surface that is open.

Specifically, as shown in FIG. 17, the platform portion 210 of the platform unit 200E is configured as an approximately square-shaped box member having an open section 215a on the front side thereof. The open section 215a is configured at a size that allows the fitting unit 100E to be inserted thereinto, and a containment chamber 215 having a size large enough to contain the fitting unit 100E is provided within the platform portion 210.

As shown in FIG. 17, during the stored state, the fitting unit 100E is inserted into the stated containment chamber 215 of the platform unit 200E through the open section 215a, and thus the fitting unit 100E is stored within the platform unit 200E. Note that in order to facilitate the storage of the fitting unit 100E in the platform unit 200E, it is preferable for the configuration to be such that the connection cable 40 for connecting the fitting unit 100E and the platform unit 200E (see FIG. 3 and so on) is detachable from at least one of the fitting unit 100E and the platform unit 200E.

With the body fat measurement device 1E according to the present embodiment as described thus far, the same effects as the effects described in the aforementioned first embodiment of the present invention can be achieved; furthermore, the configuration is such that a major portion of the fitting unit 100E is contained within the platform unit 200E during the stored state, which prevents the fitting unit 100E from being damaged during storage.

Sixth Embodiment

Figure 18:
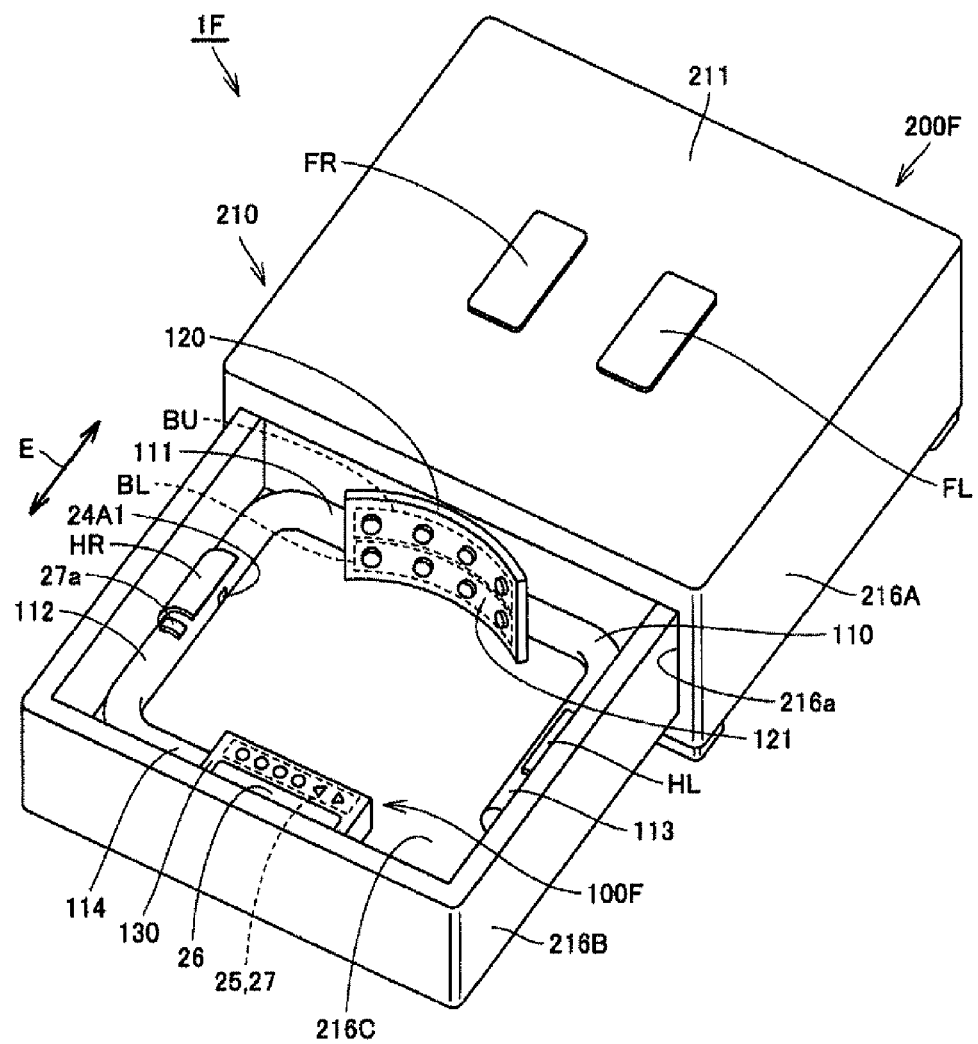
FIG. 18 is a perspective view illustrating a storage structure for a body fat measurement device according to a sixth embodiment of the present invention.

FIG. 18 is a perspective view illustrating a storage structure for a body fat measurement device according to a sixth embodiment of the present invention. Next, the structure of the body fat measurement device according to the present embodiment will be described in detail with reference to FIG. 18. Note that the fundamentals of the measurement performed by the body fat measurement device, the computation processes executed by the control unit, and so on according to the present embodiment are the same as those of the body fat measurement device according to the aforementioned first embodiment of the present invention.

As shown in FIG. 18, a body fat measurement device 1F according to the present embodiment includes, like the body fat measurement device 1A according to the aforementioned first embodiment of the present invention, a fitting unit 100F having a frame shape capable of being disposed so as to surround the trunk area of the measurement subject in a fitted state, and a platform unit 200F shaped as a platform on which the measurement subject can stand. Here, the body fat measurement device 1F according to the present embodiment differs from the body fat measurement device 1A according to the aforementioned first embodiment of the present invention in that there are no support portions positioned so as to protrude from the peripheral sides of the platform unit 200F, and instead, the platform portion 210 of the platform unit 200F is configured as a box member having a drawer that can be pulled out and pushed in.

Specifically, as shown in FIG. 18, the platform portion 210 of the platform unit 200F includes an approximately square-shaped box portion 216A having an open section 216a on the front side thereof, and a drawer 216B, whose top surface is open, configured so that the drawer 216B can be pushed in and pulled out via the open section 216a. A containment chamber 216C having a size that can contain the fitting unit 100F is provided within the drawer 216B.

As shown in FIG. 18, during the stored state, the fitting unit 100F is contained within the stated containment chamber 216C of the drawer 216B, and the drawer 216B is then inserted into the box portion 216A, thus storing the fitting unit 100F within the platform unit 200F. Through this, the fitting unit 100F is stored within the platform unit 200F without being exposed to the exterior. Note that in order to facilitate the storage of the fitting unit 100F in the platform unit 200F, it is preferable for the configuration to be such that the connection cable 40 for connecting the fitting unit 100F and the platform unit 200F (see FIG. 3 and so on) is detachable from at least one of the fitting unit 100F and the platform unit 200F.

With the body fat measurement device 1F according to the present embodiment as described thus far, the same effects as the effects described in the aforementioned first embodiment of the present invention can be achieved; furthermore, the configuration is such that the fitting unit 100F is contained within the platform unit 200F during the stored state, which prevents the fitting unit 100F from being damaged during storage.

Seventh Embodiment

Figure 19:
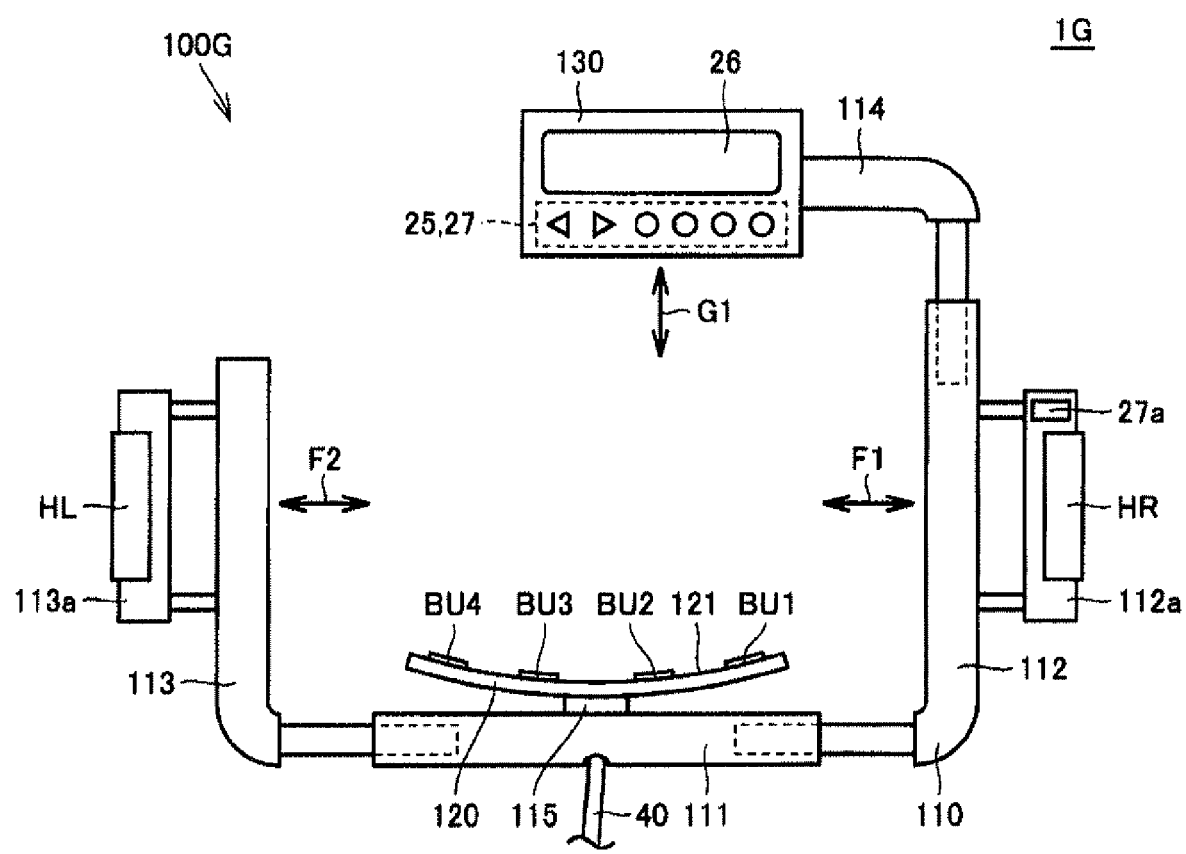
FIG. 19 is a top view of a fitting unit of the body fat measurement device according to a seventh embodiment of the present invention.
Figure 20:
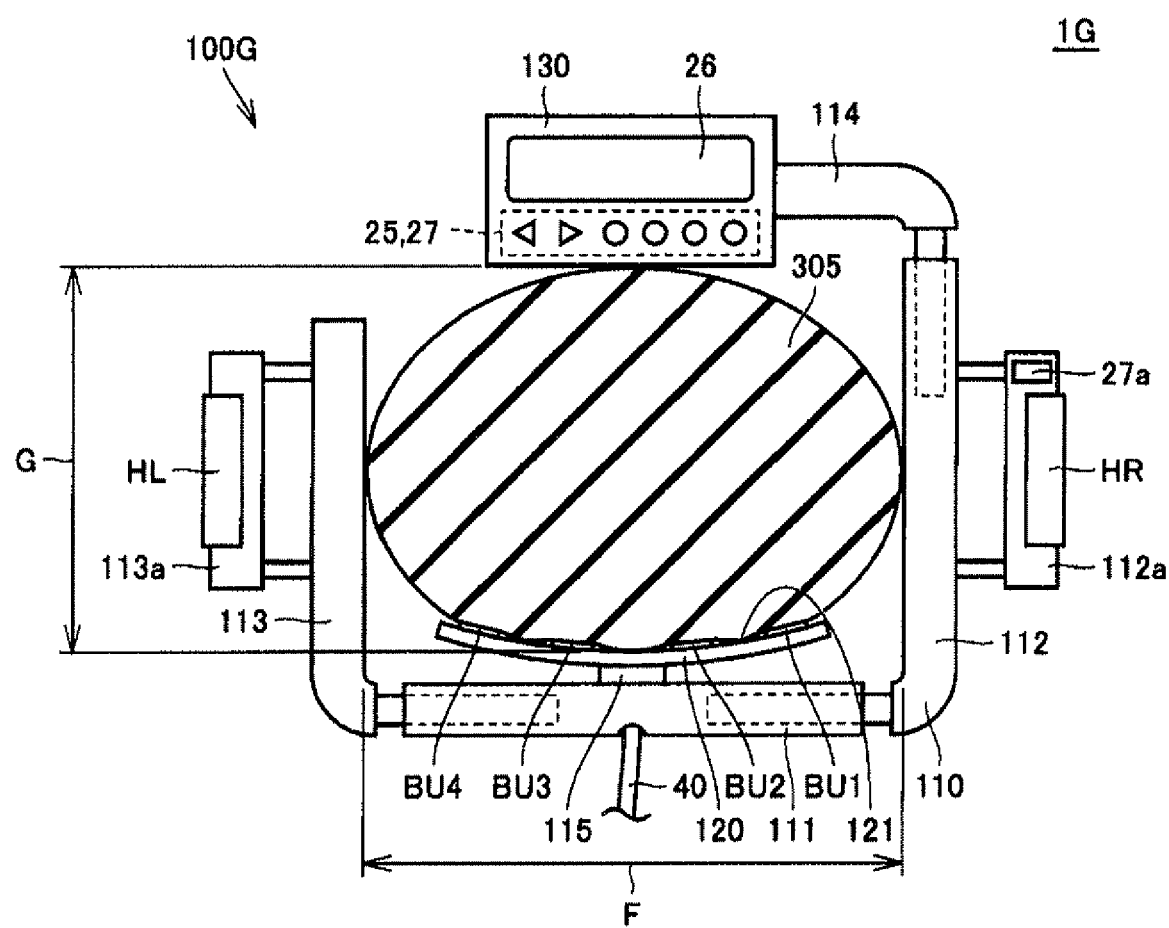
FIG. 20 is a diagram illustrating a fitted state of the fitting unit of the body fat measurement device according to the seventh embodiment of the present invention.

FIG. 19 is a top view of a fitting unit of a body fat measurement device according to a seventh embodiment of the present invention, and FIG. 20 is a diagram illustrating a fitted state of the fitting unit of the body fat measurement device according to the present embodiment. First, details of the structure of the fitting unit of the body fat measurement device according to the present embodiment, and a fitted state of the fitting unit, will be described with reference to FIGS. 19 and 20. Note that the fundamentals of the measurement performed by the body fat measurement device, the computation processes executed by the control unit, and so on according to the present embodiment are the same as those of the body fat measurement device according to the aforementioned first embodiment of the present invention.

Figure 21:
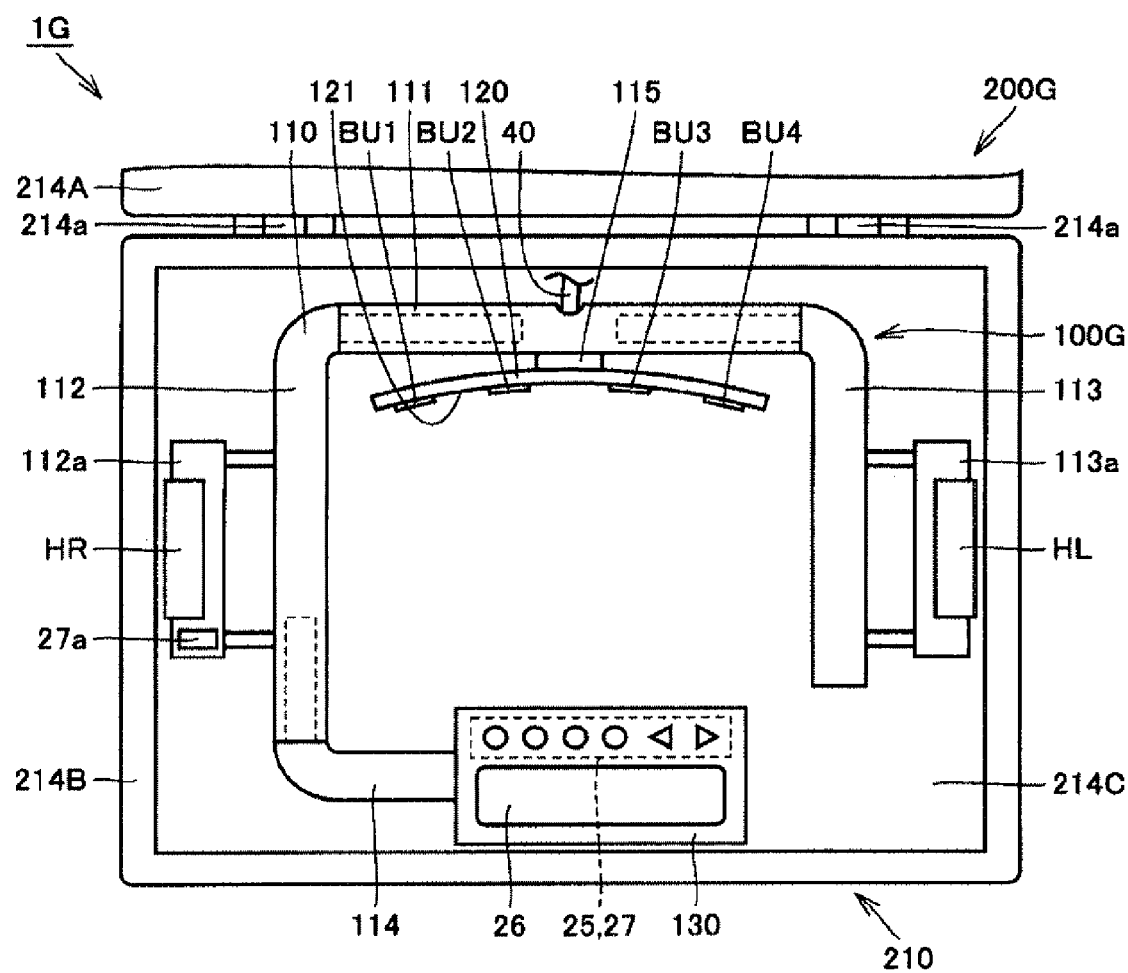
FIG. 21 is a top view illustrating a storage structure for the body fat measurement device according to the seventh embodiment of the present invention.

As shown in FIG. 19 through 21, a body fat measurement device 1G according to the present embodiment includes, like the body fat measurement device 1A according to the aforementioned first embodiment of the present invention, a fitting unit 100G having a frame shape capable of being disposed so as to surround the trunk area of the measurement subject in a fitted state, and a platform unit 200G (see FIG. 21) shaped as a platform on which the measurement subject can stand.

As shown in FIG. 19, the fitting unit 100G of the body fat measurement device 1G according to the present embodiment is configured so that the rear frame portion 111, the right-side frame portion 112, the left-side frame portion 113, and the front frame portion 114 of the frame member 110 are divided into individual units, and the rear frame portion 111, the right-side frame portion 112, the left-side frame portion 113, and the front frame portion 114 are each linked to their respective adjacent frame portions so as to be capable of moving relative thereto.

To be more specific, the right-side frame portion 112 is configured so as to be capable of moving relative to the rear frame portion 111 in the direction of an arrow F1 shown in FIG. 19, the left-side frame portion 113 is configured so as to be capable of moving relative to the rear frame portion 111 in the direction of an arrow F2 shown in FIG. 19, and the front frame portion 114 is configured so as to be capable of moving relative to the right-side frame portion 112 in the direction of an arrow G1 shown in FIG. 19.

Furthermore, with the body fat measurement device 1G according to the present embodiment, handle portions 112a and 113a are provided projecting outward from the right-side frame portion 112 and the left-side frame portion 113, respectively, and the hand electrodes HR and HL are provided on the handle portions 112a and 113a, respectively, in an exposed state.

Here, the body fat measurement device 1G according to the present embodiment does not include the non-contact optical sensor provided in the body fat measurement device 1A according to the aforementioned first embodiment of the present invention; instead, a movement amount detection sensor that serves as the trunk area width detection unit 24A and detects the relative amount of movement between the stated right-side frame portion 112 and left-side frame portion 113 and the rear frame portion 111, and a movement amount detection sensor that serves as the trunk area depth detection unit 24B and detects the relative amount of movement between the stated front frame portion 114 and the right-side frame portion 112, are provided in the fitting unit 100A. A variety of elements, including various types of encoders such as rotary encoders, optical sensors, magnetic sensors, and so on, can be used as the movement amount detection sensors.

As shown in FIG. 20, when the fitting unit 100G is in the fitted state, the trunk area 305 of the measurement subject is surrounded by the frame member 110, and the abdominal area, back area, and both side areas of the trunk area 305 are in contact with the fitting unit 100G.

In order to achieve this state, the measurement subject grips the handle portions 112a and 113a with his/her right hand and left hand, respectively, so that the palms of his/her right hand and left hand make contact with the hand electrodes HR and. HL, respectively; while maintaining this grip, the measurement subject adjusts the position of the fitting unit 100G so that the front surface 121 of the electrode support member 120 provided in the fitting unit 100G makes contact with his/her back area surface.

At this time, the measurement subject moves the right-side frame portion 112 and the left-side frame portion 113 so that an inner side area of the right-side frame portion 112 and an inner side area of the left-side frame portion 113 make contact with both sides of the trunk area 305 (that is, both flanks), respectively; the measurement subject then releases one hand, moves the front frame portion 114 so that the rear surface of the display unit portion 130 makes contact with a front area of the trunk area (in other words, the abdominal area), and then returns the released hand back to its original position.

Furthermore, at this time, the measurement subject adjusts the orientation of the fitting unit 100G so that the fitting unit 100G is level. As a result, the fitting unit 100G enters the fitted state shown in FIG. 15, and the measurement of body fat mass can be started.

Here, assuming that the positions of the right-side frame portion 112, the left-side frame portion 113, and the front frame portion 114 shown in FIG. 19 are the starting points, the amounts by which the right-side frame portion 112, the left-side frame portion 113, and the front frame portion 114 move from the starting points shown in FIG. 19 until those frame portions reach the positions shown in FIG. 20 are measured by the stated movement amount detection sensors, and thus, as shown in FIG. 20, the width 2a of the trunk area is calculated as a distance F, and the depth 2b of the trunk area is calculated as a distance G.

FIG. 21 is a top view illustrating a storage structure for the body fat measurement device according to the present embodiment. Next, the storage structure of the body fat measurement device according to the present embodiment will be described with reference to FIG. 21.

As shown in FIG. 21, the platform unit 200G has the same structure as the platform unit 200D described in the aforementioned fourth embodiment of the present invention (see FIG. 16), and the platform unit 2000 is configured as a box member that can be opened and closed. In other words, the platform portion 210 of the platform unit 2000 is configured of the cover plate portion 214A that configures the top surface of the platform portion 210 and the approximately square-shaped box portion 214B whose top surface is open, and the cover plate portion 214A is attached to the box portion 214B by the hinges 214a so as to be capable of pivoting. Note that the containment chamber 214C is provided within the box portion 214B.

Here, with the body fat measurement device 1G according to the present embodiment, as described above, the frame portions of the fitting unit 100G (that is, the rear frame portion 111, the right-side frame portion 112, the left-side frame portion 113, and the front frame portion 114) are configured so as to be capable of moving relative to each other, and thus the shape of the fitting unit 100G is put into a reduced state (that is, the state shown in FIG. 21) by moving the frame portions, after which the fitting unit 100G is placed within the containment chamber 214C. In other words, the size of the containment chamber 214C can be reduced to a size that can contain the fitting unit 100G when the fitting unit 100G has been reduced to its minimum size. According to such a configuration, the size of the platform unit 200G can be greatly reduced even when a configuration that contains the fitting unit 100G within the platform unit 200G is employed.

Accordingly, with the body fat measurement device 1G according to the present embodiment as described thus far, the same effects as the effects of the aforementioned first and fourth embodiments of the present invention can be achieved, and furthermore, the device profile can be reduced when in the stored state.

Eighth Embodiment

Figure 22:
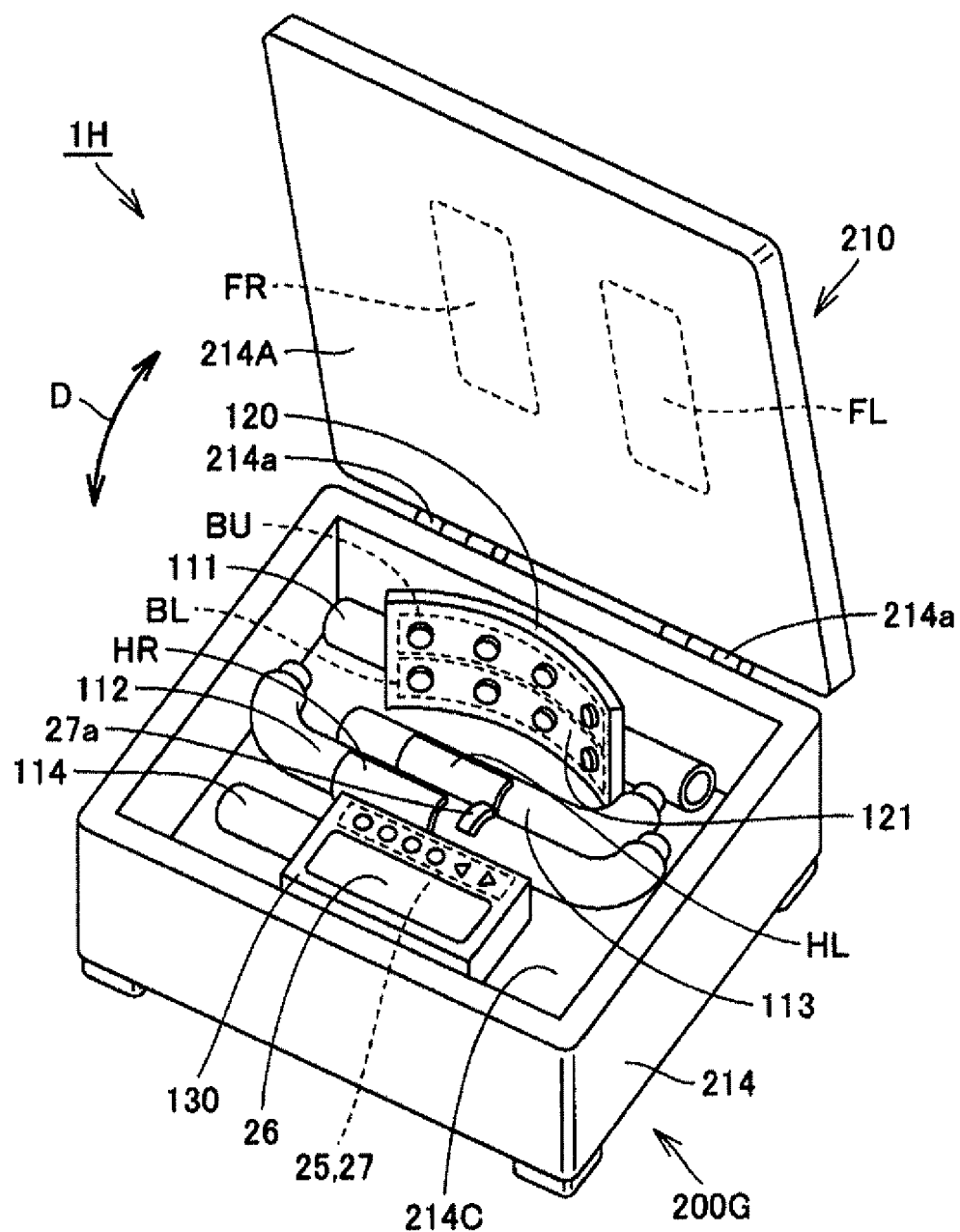
FIG. 22 is a perspective view illustrating a storage structure for a body fat measurement device according to an eighth embodiment of the present invention.

FIG. 22 is a perspective view illustrating a storage structure for a body fat is measurement device according to an eighth embodiment of the present invention. Next, the storage structure of the body fat measurement device according to the present embodiment will be described with reference to FIG. 22. Note that the fundamentals of the measurement performed by the body fat measurement device, the computation processes executed by the control unit, and so on according to the present embodiment are the same as those of the body fat measurement device according to the aforementioned first embodiment of the present invention.

As shown in FIG. 22, a body fat measurement device 1H according to the present embodiment includes, like the body fat measurement device 1A according to the aforementioned first embodiment of the present invention, a fitting unit 100H having a frame shape capable of being disposed so as to surround the trunk area of the measurement subject in a fitted state, and a platform unit 200H shaped as a platform on which the measurement subject can stand.

However, the body fat measurement device 1H according to the present embodiment differs from the body fat measurement device 1A according to the aforementioned first embodiment of the present invention in that the fitting unit 100H is configured so as to be capable of being broken down into multiple parts. Specifically, as shown in FIG. 22, the fitting unit 100H of the body fat measurement device 1H according to the present embodiment is configured so that the frame member 110 is divided and can thus be broken down into the rear frame portion 111, the right-side frame portion 112, the left-side frame portion 113, and the front frame portion 114.

Here, as shown in FIG. 22, the platform unit 200H has the same structure as the platform unit 200D described in the aforementioned fourth embodiment of the present invention (see FIG. 16), and the platform unit 200H is configured as a box member that can be opened and closed. In other words, the platform portion 210 of the platform unit 200H is configured of the cover plate portion 214A that configures the top surface of the platform portion 210 and the approximately square-shaped box portion 214B whose top surface is open, and the cover plate portion 214A is attached to the box portion 214B by the hinges 214a so as to be capable of pivoting. Note that the containment chamber 214C is provided within the box portion 214B.

As described thus far, with the body fat measurement device 1H according to the present embodiment, the frame portions of the fitting unit 100H (in other words, the rear frame portion 111, the right-side frame portion 112, the left-side frame portion 113, and the front frame portion 114) are configured so as to be capable of being broken down, and the fitting unit 100H is stored within the containment chamber 214C with the frame portions in the broken-down state (that is, the state shown in FIG. 22). In other words, the size of the containment chamber 214C can be reduced to a size that can contain the portions of the fitting unit 100H when the fitting unit 100H has been broken down. According to such a configuration, the size of the platform unit 200H can be greatly reduced even when a configuration that contains the fitting unit 100H within the platform unit 200H is employed.

Accordingly, with the body fat measurement device 1H according to the present embodiment as described thus far, the same effects as the effects of the aforementioned first and fourth embodiments of the present invention can be achieved, and furthermore, the device profile can be reduced when in the stored state.

Although the first through eighth embodiments of the present invention described above describe examples in which the hand electrodes HR and HL are respectively provided in the right-side frame portion 112 and the left-side frame portion 113 of the frame member 110 in the fitting units 100A through 100H that serve as the trunk area width measurement units, it should be noted that the hand electrodes HR and HL may be provided in the front frame portion 114 of the frame member 110, and, depending on the situation, may not be provided in the fitting unit.

In addition, although the aforementioned first through eighth embodiments of the present invention have described examples in which part of the frame member 110 in the fitting units 100A through 100H that serve as the trunk area width measurement units is not continuous, the configuration may be such that the shape is continuous.

In addition, although the aforementioned first through eighth embodiments of the present invention have described examples in which the frame member 110 of the fitting units 100A through 100H serving as the trunk area width measurement units has a frame-shaped outer shape that is approximately rectangular when viewed from above, the frame member 110 may be configured having a different shape, such as a ring shape, a U shape, a C shape, or the like.

In addition, because the aforementioned first through eighth embodiments of the present invention are configured so as to include the platform units 200A through 200H, the platform units 200A through 200H may be provided with a body weight measurement function. In other words, the configuration may be such that a load cell or the like that serves as a body weight measurement unit for detecting a load on the platform unit 200 is provided, which enables the weight of the measurement subject standing on the platform unit 200 to be measured by the body weight measurement unit. In this case, if the configuration is such that body weight information measured by the body weight measurement unit provided in the platform unit 200 is inputted into the control unit 10, the actual measured body weight of the target subject can be used as measurement subject information in the various types of computation processes.

In addition, although the aforementioned first through eighth embodiments of the present invention describe examples in which the computation processes are configured so as to calculate the visceral fat cross-sectional area as the visceral fat mass and the subcutaneous fat cross-sectional area as the subcutaneous fat mass, the computation processes may be configured so that a different indicator than the visceral fat cross-sectional area, such as the visceral fat volume, visceral fat weight, visceral fat level, or the like is calculated as the visceral fat mass, and a different indicator than the subcutaneous fat cross-sectional area, such as the subcutaneous fat volume, subcutaneous fat weight, subcutaneous fat level, or the like is calculated as the subcutaneous fat mass.

In addition, although the aforementioned first through eighth embodiments of the present invention describe examples in which the configuration is such that both the visceral fat cross-sectional area and the subcutaneous fat cross-sectional area are calculated and displayed, the configuration may be such that only one of these indicators is displayed, or that only the subcutaneous fat cross-sectional area is calculated and displayed. Furthermore, the configuration may be such that various types of body composition information aside from the visceral fat cross-sectional area and the subcutaneous fat cross-sectional area (for example, the body fat mass, area-by-area fat mass, fat-free mass, and so on) are calculated and displayed.

In this manner, the embodiments disclosed herein are to be understood in all ways as exemplary and in no ways limiting. The technical scope of the present invention is defined by the appended claims, and all variations that fall within the meaning and range of equivalency of the claims are intended to be embraced therein.

REFERENCE SIGNS LIST 1A-1H body fat measurement device
10 control unit
11 computation processing unit
12 body impedance measurement unit
13 body shape information measurement unit
14 body composition information obtainment unit
14a visceral fat mass calculation unit
14b subcutaneous fat mass calculation unit
21 constant current generation unit
22 terminal switching unit
23 potential difference detection unit
24A trunk area width detection unit
24B trunk area depth detection unit
24A1, 24A2, 24B1 detection window portion
25 measurement subject information input unit
26 display unit 27 operating unit
27a measure button
28 power source unit
29 memory unit
40 connection cable
100A-100H fitting unit
110 frame member
111 rear frame portion
112 right-side frame portion
112a handle portion
113 left-side frame portion
113a handle portion
114 front frame portion
115 connection portion
120 electrode support member
121 front surface
130 display unit portion
200A-200H platform unit
210 platform portion
211 top surface
212 step section
212a electrode support member housing step section
212b display unit portion housing step section
213 recess section
213a electrode support member housing recess section
213b display unit portion housing recess section
214A cover plate portion
214B box portion
214C containment chamber
214a hinge
215 containment chamber
215a open section
216A box portion
216B drawer
216C containment chamber
216a open section
220 support portion
300 measurement subject
301 right foot
302 left foot
303 right hand
304 left hand
305 trunk area
HR, HL hand electrode
BU1-BU4, BL1-BL4, BA1-BA4 back area electrode
FR, FL foot electrode

The invention claimed is:

1. A body fat measurement device comprising:
multiple electrodes for making contact with predetermined areas of a surface of a measurement subject's body, wherein the multiple electrodes include at least lower limb electrodes for making contact with surfaces of the measurement subject's lower limbs;
a body impedance measurement unit that measures a body impedance of the measurement subject's body using the multiple electrodes;
a trunk area width detection unit for detecting a trunk area width and a trunk area depth of the measurement subject; and
a body fat mass calculation unit programmed to calculate a body fat mass based on the body impedance measured by the body impedance measurement unit and the trunk area width and trunk area depth detected by the trunk area width detection unit,
a frame-shaped trunk area width measurement unit in which the trunk area width detection unit is provided and that is capable of being disposed so as to substantially surround four sides of the measurement subject's trunk area, wherein the frame-shaped trunk area width measurement unit defines a hollow opening area into which the measurement subject's trunk area is inserted;
a platform unit for bringing the lower limb electrodes into contact with the soles of the measurement subject's feet when the measurement subject steps onto the platform unit,
wherein the trunk area width measurement unit can be attached to and removed from the platform unit so as to take on a stored state, in which the trunk area width measurement unit is stored with the platform unit, and an unstored state, in which the trunk area width measurement unit is removed from the platform unit, and
at least part of the platform unit is, during the stored state, contained within the hollow opening area of the trunk area width measurement unit.

2. The body fat measurement device according to claim 1, wherein a support portion for supporting the trunk area width measurement unit is provided so as to protrude from a peripheral surface of the platform unit.

3. The body fat measurement device according to claim 1, wherein a step section that contains at least part of the trunk area width measurement unit during the stored state is provided in a peripheral edge of a top surface of the platform unit.

4. The body fat measurement device according to claim 1, wherein a recess section that contains at least part of the trunk area width measurement unit during the stored state is provided in an area of a top surface of the platform unit that excludes a peripheral edge.

5. The body fat measurement device according to claim 1, wherein the trunk area width detection unit is configured as a non-contact range sensor provided on at least one of a right side portion and a left side portion of the trunk area width measurement unit and a non-contact range sensor provided on a front portion of the trunk area width measurement unit.

6. The body fat measurement device according to claim 1, wherein at least one of a right side portion or a left side portion of the trunk area width measurement unit can move along the measurement subject's trunk area width direction;
at least one of a front portion or a rear portion of the trunk area width measurement unit can move along the measurement subject's trunk area depth direction; and
the trunk area width detection unit is configured as a movement amount detection sensor that detects the amount by which the portion of the trunk area width measurement unit that can move has moved.

7. The body fat measurement device according to claim 1, wherein the multiple electrodes further include back area electrodes for making contact with a surface of a back area that corresponds to an area of the measurement subject's trunk area on the back side thereof; and
the back area electrodes are provided on the trunk area width measurement unit in an exposed state.

8. The body fat measurement device according to claim 7, wherein the back area electrodes are provided on a rear portion of the trunk area width measurement unit so that a contact surface of the back area electrodes faces forward toward the back area surface in a fitted state, and the trunk area width measurement unit surrounds the subject's trunk area.

9. The body fat measurement device according to claim 1, wherein the multiple electrodes further include upper limb electrodes for making contact with surfaces of the measurement subject's upper limbs; and
the upper limb electrodes are provided on a surface of the trunk area width measurement unit in an exposed state.

10. The body fat measurement device according to claim 9, wherein the upper limb electrodes are provided on at least one of a front portion, a right side portion, or a left side portion that exclude the rear portion of the trunk area width measurement unit.

11. The body fat measurement device according to claim 1, wherein the platform unit includes a body weight measurement unit that measures the weight of the measurement subject.

12. The body fat measurement device according to claim 1, wherein the body fat mass calculation unit includes at least one of a visceral fat mass calculation unit programmed to calculate the visceral fat mass of the measurement subject or a subcutaneous fat mass calculation unit programmed to calculate the subcutaneous fat mass of the measurement subject.

\* \* \* \* \*